United States Patent [19]
Yoon

[11] Patent Number: 5,836,953
[45] Date of Patent: Nov. 17, 1998

[54] MULTIFUNCTIONAL DEVICES HAVING LOOP CONFIGURED PORTIONS AND COLLECTION SYSTEMS FOR ENDOSCOPIC SURGICAL PROCEDURES AND METHODS THEREFOR

[76] Inventor: InBae Yoon, 2101 Highland Ridge Dr., Phoenix, Md. 21131

[21] Appl. No.: 982,334

[22] Filed: Dec. 2, 1997

Related U.S. Application Data

[60] Continuation of Ser. No. 546,750, Oct. 23, 1995, Pat. No. 5,755,724, which is a division of Ser. No. 287,007, Aug. 8, 1994, Pat. No. 5,556,376, said Ser. No. 287,007, is a continuation-in-part of Ser. No. 45,768, Apr. 14, 1993, Pat. No. 5,451,204, which is a continuation-in-part of Ser. No. 600,775, Oct. 23, 1990, Pat. No. 5,374,261, which is a continuation-in-part of Ser. No. 596,937, Oct. 15, 1990, abandoned, said Ser. No. 45,768, is a continuation-in-part of Ser. No. 789,599, Nov. 8, 1991, abandoned, said Ser. No. 789,599, is a division of Ser. No. 556,081, Jul. 24, 1990, Pat. No. 5,074,840, said Ser. No. 600,775, is a continuation-in-part of Ser. No. 556,081, Jul. 24, 1990, which is a continuation-in-part of Ser. No. 596,937, Oct. 15, 1990, abandoned, which is a continuation-in-part of Ser. No. 222,776, Jul. 22, 1988, abandoned.

[51] Int. Cl.$^6$ .................... A61B 17/24; A61B 17/26
[52] U.S. Cl. .................. 606/114; 606/110; 606/127; 606/170; 600/565
[58] Field of Search ................... 606/110, 114, 606/127, 128, 151, 159, 160, 170, 198; 604/104, 105; 600/562, 564, 565, 566, 567

[56] References Cited

U.S. PATENT DOCUMENTS

| | | |
|---|---|---|
| 4,850,354 | 7/1989 | McGurk-Burleson et al. . |
| 5,037,379 | 8/1991 | Clayman et al. . |
| 5,074,867 | 12/1991 | Wilk . |
| 5,126,334 | 6/1992 | Fitt et al. . |
| 5,147,371 | 9/1992 | Washington et al. . |
| 5,176,687 | 1/1993 | Hasson et al. . |
| 5,190,561 | 3/1993 | Graber . |
| 5,192,284 | 3/1993 | Pleatman . |
| 5,197,968 | 3/1993 | Clement . |
| 5,215,521 | 6/1993 | Cochran et al. . |
| 5,275,610 | 1/1994 | Eberbach . |
| 5,320,627 | 6/1994 | Sorensen et al. ............... 606/128 |
| 5,354,303 | 10/1994 | Spaeth et al. . |
| 5,370,647 | 12/1994 | Gaber et al. . |
| 5,417,697 | 5/1995 | Wilk et al. . |
| 5,443,472 | 8/1995 | Li . |
| 5,556,376 | 9/1996 | Yoon . |

*Primary Examiner*—Richard J. Apley
*Assistant Examiner*—Justine R. Yu

[57] ABSTRACT

A collection system for collecting substances within the body of a patient in operative procedures wherein access to an internal operative site in the patient's body is gained through a narrow portal in the patient's body includes a cutter and a collection bag attached to a distal end of the cutter. The cutter has the distal end for being disposed at the operative site through the portal, a proximal end for being disposed external of the patient's body, a cutting edge at the distal end for cutting anatomical tissue and a handle at the proximal end for moving the cutting edge to cut the anatomical tissue. The collection bag is disposed over the distal end of the cutter and has a closed distal end, a proximal end fixedly attached to the cutter, an interior receiving the cutting edge therein and a selectively openable, selectively closable access slot providing communication with the interior of the collection bag from external thereof. The collection bag has a collapsed position facilitating introduction of the collection bag and the distal end of the cutter at the operative site through the portal. The collection bag is movable, from external of the patient's body, from the collapsed position to an expanded position after being introduced at the operative site to allow substances to be introduced in the interior of the collection bag through the access slot to be cut by the cutter. The cutter has a lumen between the distal and proximal ends thereof connectable with a source of suction external of the patient's body to withdraw substances from the interior of the collection bag while the collection bag remains at the operative site.

10 Claims, 9 Drawing Sheets

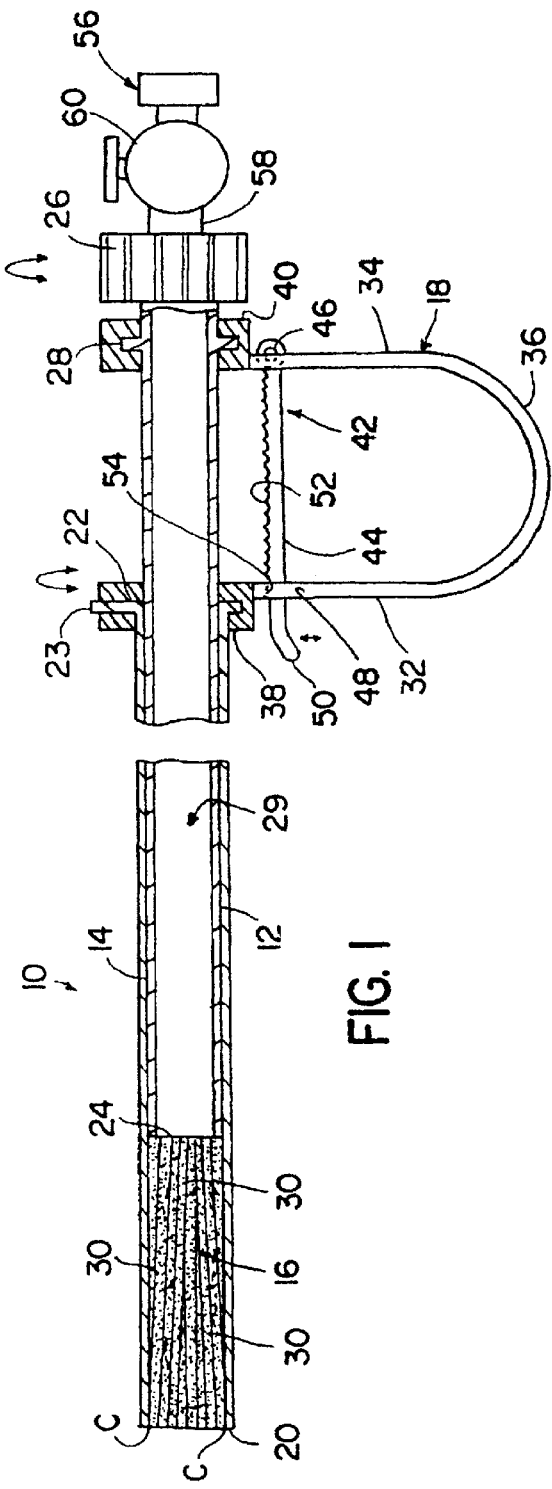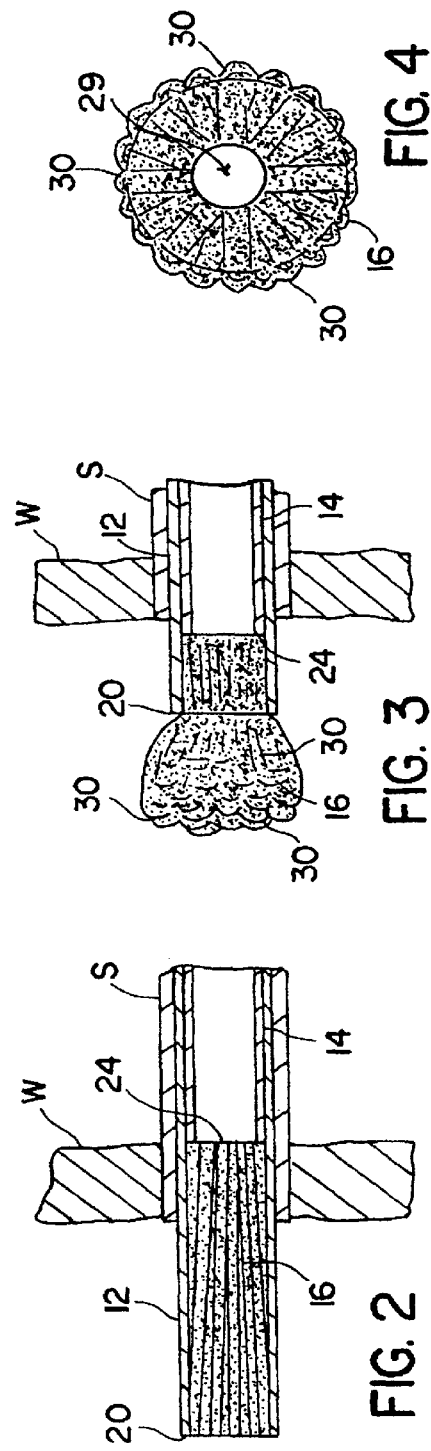

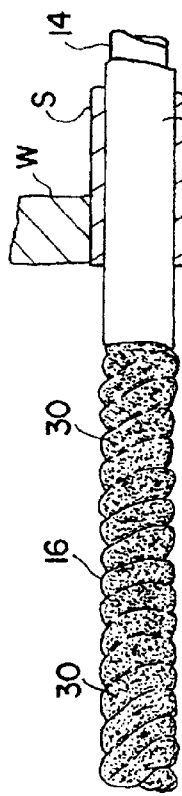
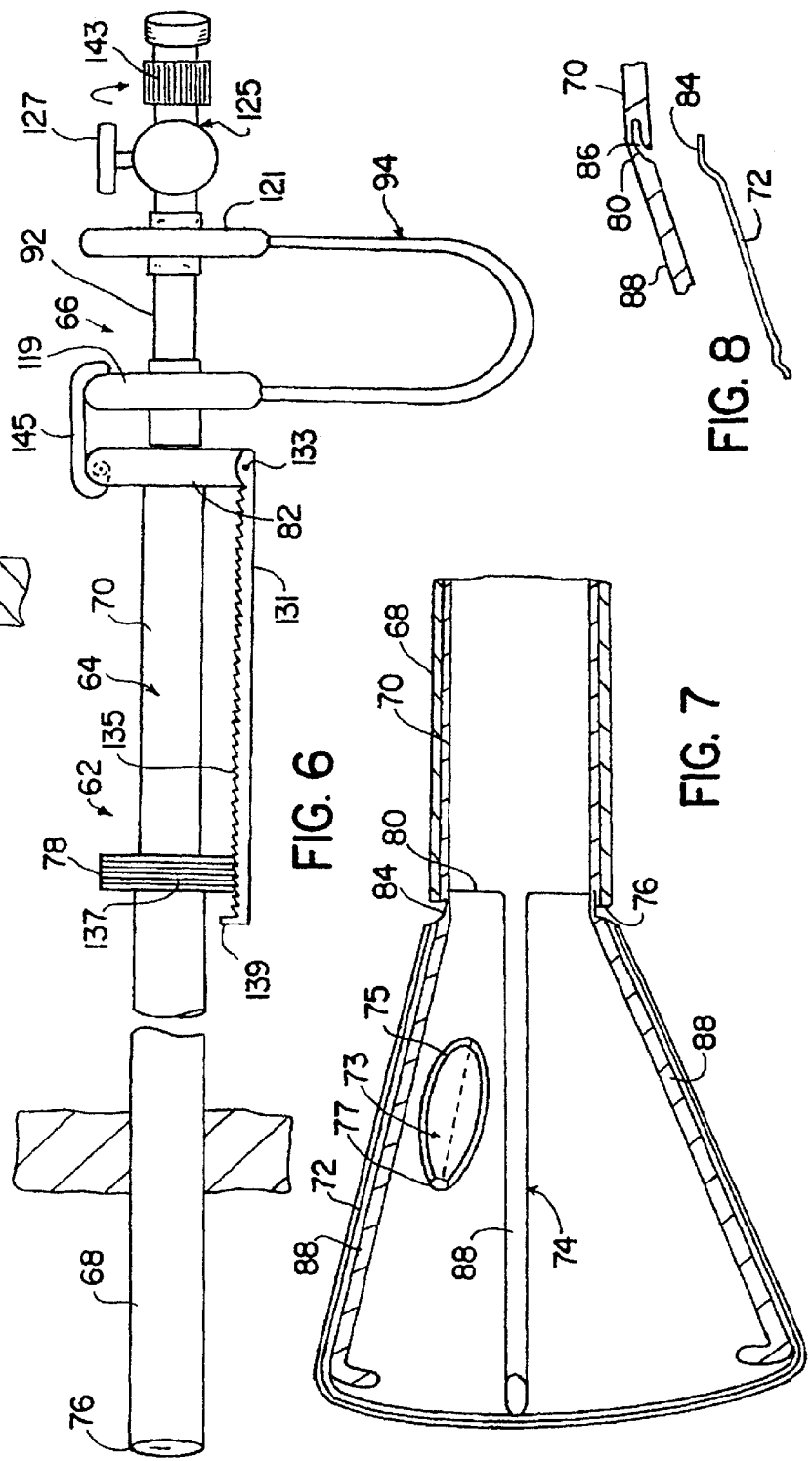
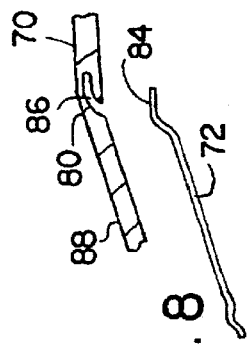
FIG. 5
FIG. 6
FIG. 7
FIG. 8

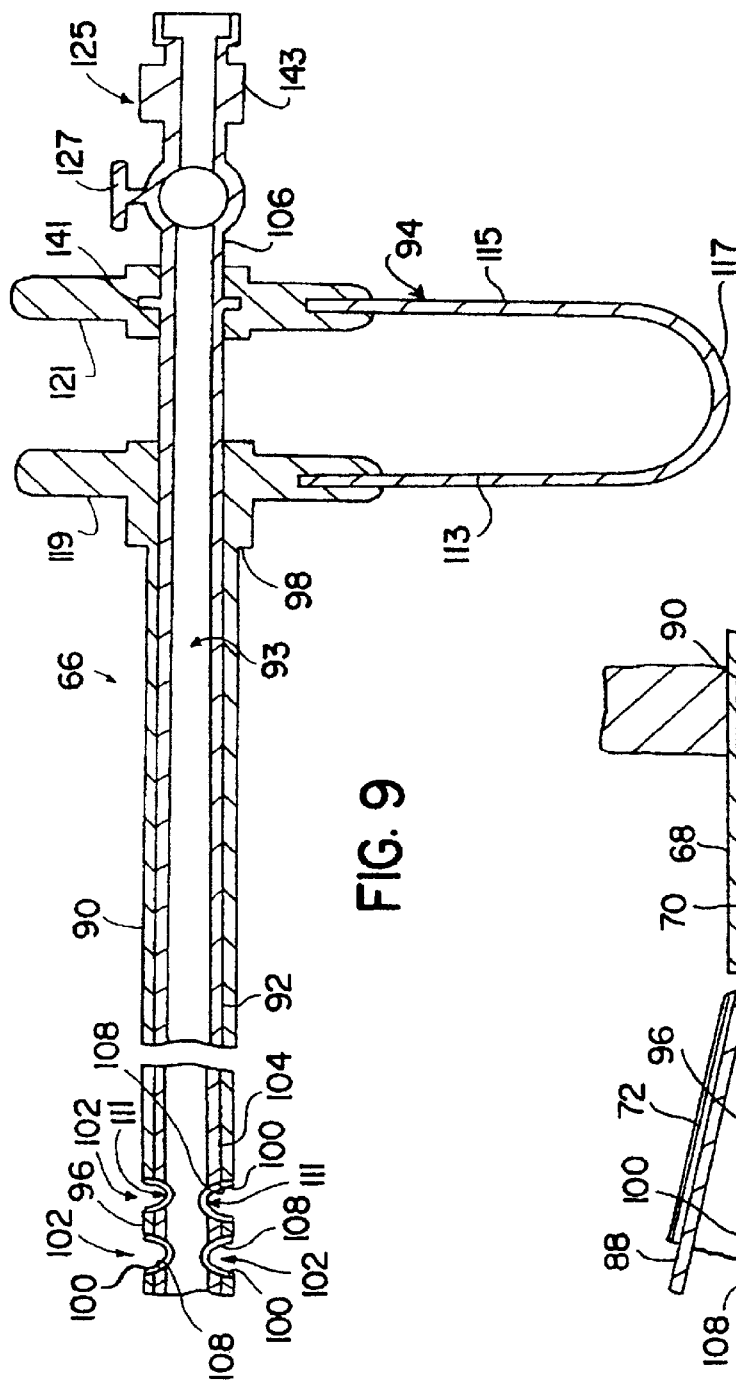
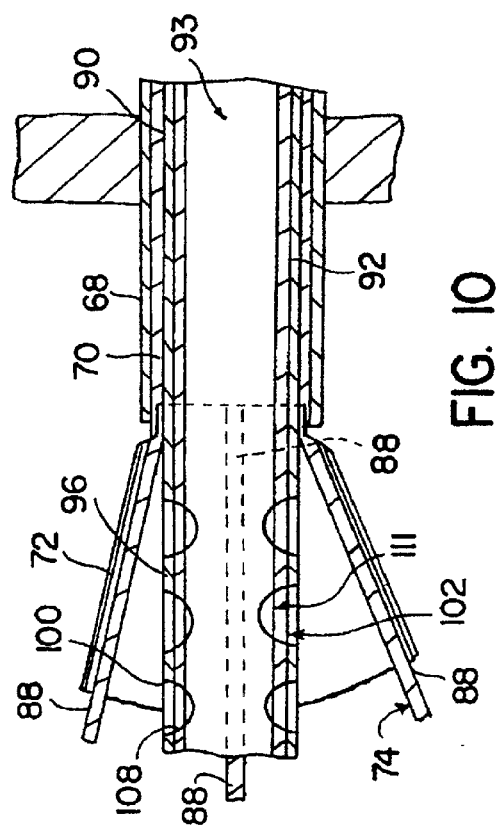
FIG. 9
FIG. 10

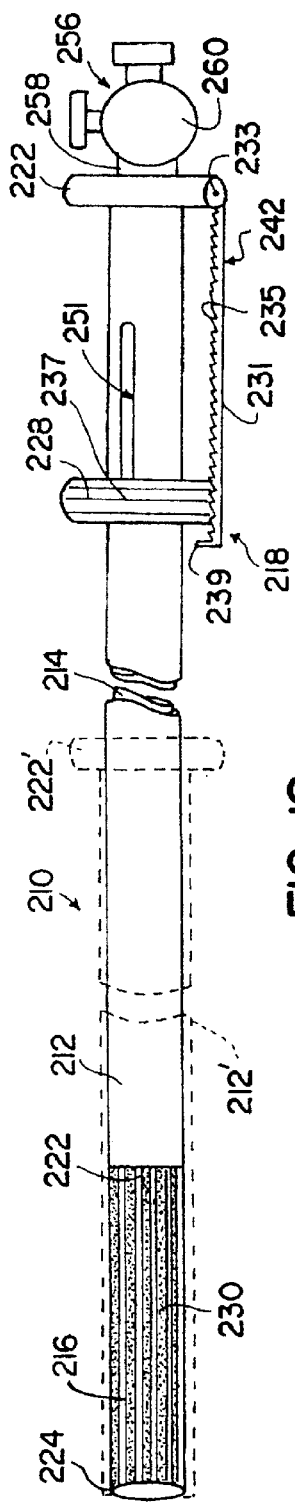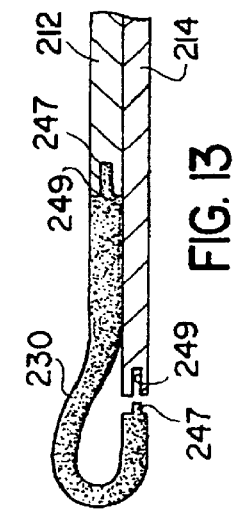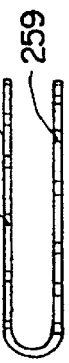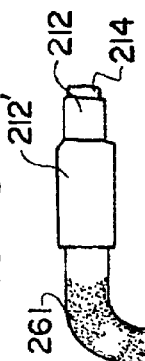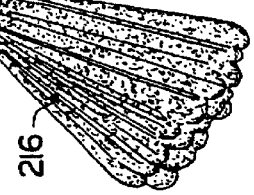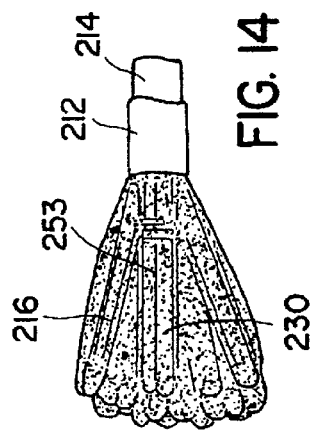

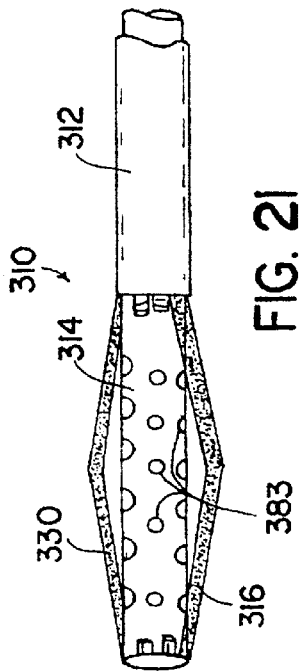
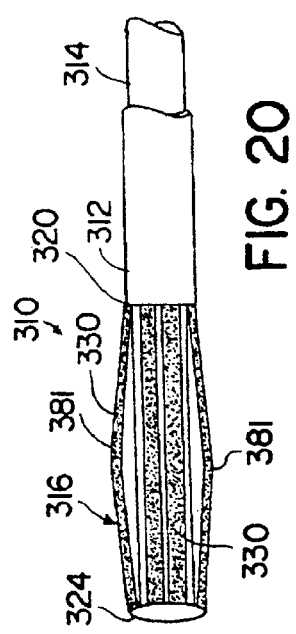
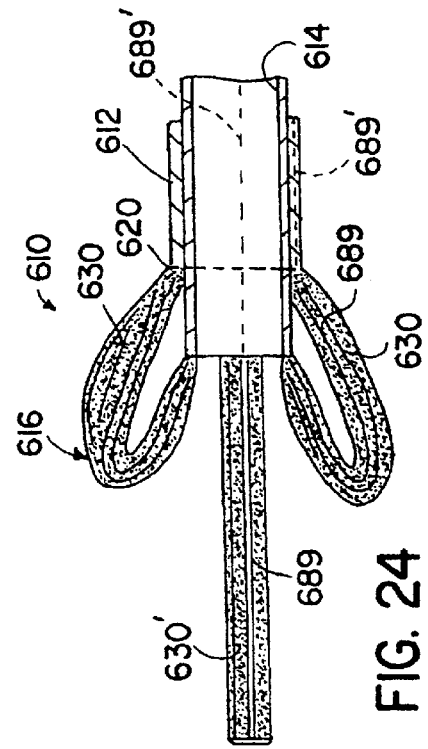
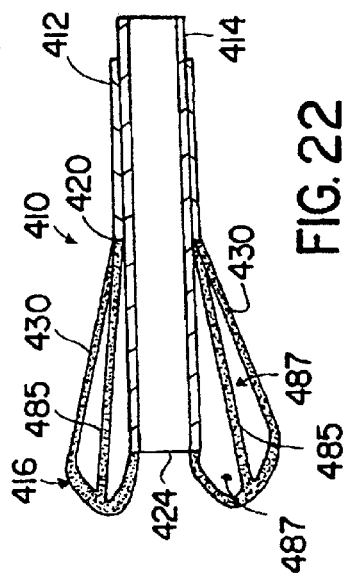
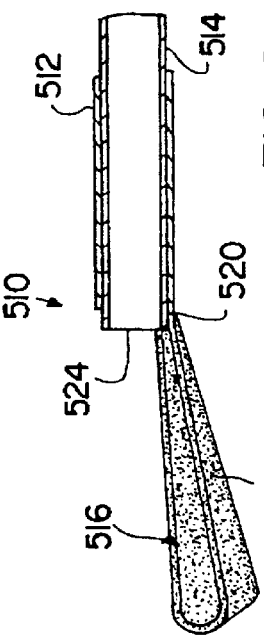

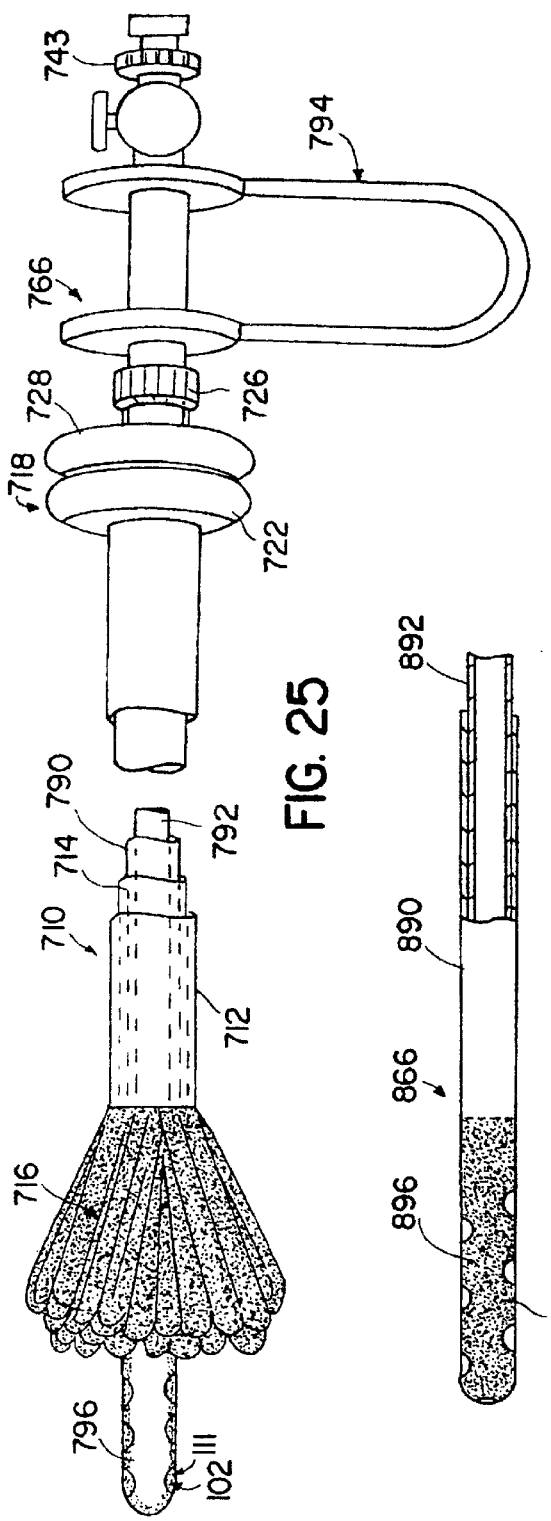
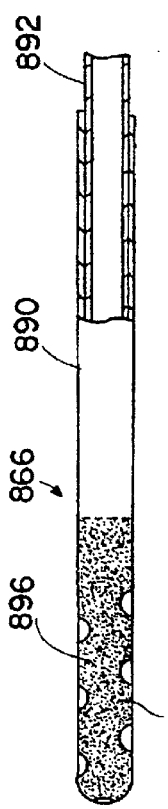
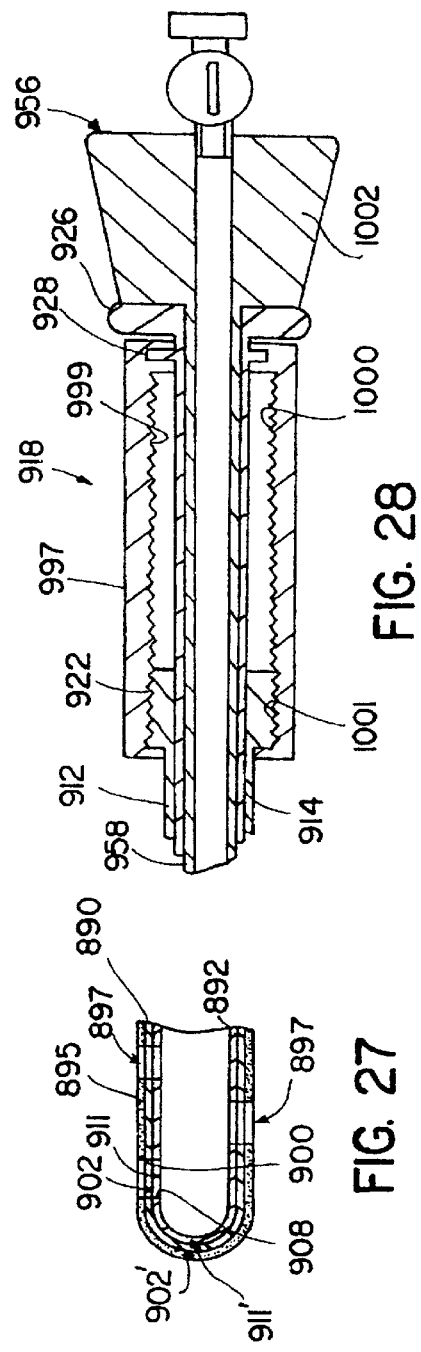
FIG. 25
FIG. 26
FIG. 27
FIG. 28

MULTIFUNCTIONAL DEVICES HAVING LOOP CONFIGURED PORTIONS AND COLLECTION SYSTEMS FOR ENDOSCOPIC SURGICAL PROCEDURES AND METHODS THEREFOR

CROSS-REFERENCE TO RELATED PATENT APPLICATIONS

This application is a continuation of application Ser. No. 08/546,750, filed Oct. 23, 1995 now U.S. Pat. No. 5,755,724, which is a division of prior application Ser. No. 08/287,007, filed Aug. 8, 1994 and now U.S. Pat. No. 5,556,376, Ser. No. 08/287,007 being a continuation-in-part of prior applications Ser. No. 08/045,768, filed Apr. 14, 1993 and now U.S. Pat. No. 5,451,204, Ser. No. 07/600,775, filed Oct. 23,1990 and now U.S. Pat. No. 5,374,261 and Ser. No. 07/596,937, filed Oct. 15, 1990 and now abandoned, Ser. No. 08/045,768 being a continuation-in-part of prior application Ser. No. 07/789,599, filed Nov. 8,1991 and now abandoned, Ser. No. 07/789,599 being a division of prior application Ser. No. 07/556,081, filed Jul. 24,1990 and now U.S. Pat. No. 5,074,840, Ser. No. 07/600,775 being a continuation-in-part of Ser. No. 07/556,081 and Ser. No. 07/596,937 being a continuation-in-part of prior application Ser. No. 07/222,776, filed Jul. 22,1988 and now abandoned.

BACKGROUND OF THE INVENTION

1. Field of the Invention

The present invention relates to endoscopic surgery and, more particularly, to devices and methods for use in endoscopic surgery to perform various functions including creating or increasing the size of a space in the body, aspiration, irrigation, wiping, cleansing, manipulating or retracting tissue or organ structures, separating adhering tissue (lysis of adhesion), dissecting tissue, isolating tissue to be treated, protecting surrounding tissue, increasing visibility for the surgeon, collecting substances in the body and miniaturizing collected substances.

2. Description of the Prior Art

Endoscopically performed operative procedures are preferred for surgery on the human body due to their least invasive nature and reduced trauma and tissue damage as compared with open surgery. While endoscopically performed operative procedures are preferred, there are obstacles to expanding endoscopy to include the various procedures currently performed with open surgery. For example, endoscopic procedures are much more difficult and dangerous to perform where tissue or organ structure cannot be adequately exposed and manipulated, surrounding tissue and organ structure cannot be protected during the operative procedure and fluids cannot be removed from the operative site. Additionally, in many endoscopic procedures, there is little or no space by which to access the operative site and introduce and maneuver instruments. Furthermore, in many endoscopic procedures, it is extremely difficult to accomplish facilitating procedures including tissue retraction and manipulation, cleansing, wiping, lysis of adhesion, tissue dissection, collection and/or miniaturization of fluids and/or tissue samples, tissue coagulation and irrigation and/or aspiration.

SUMMARY OF THE INVENTION

Accordingly, it is a primary object of the present invention to improve the efficacy and safety of endoscopic operative procedures.

Another object of the present invention is to expand the types of procedures that can be performed endoscopically.

An additional object of the present invention is to facilitate endoscopic procedures with a multifunctional device having a portion capable of being deployed in a loop configuration upon introduction of the portion in the body to perform various diverse functions.

It is also an object of the present invention to provide a method of facilitating the performance of endoscopic procedures including the steps of introducing a loop forming portion of a multifunctional device in the body in a non-deployed position and moving the loop forming portion, from externally of the body, to a deployed position forming a loop configuration.

Another object of the present invention is to facilitate endoscopic procedures with a collection system having a collection bag for being introduced in the body through a narrow portal to allow substances to be placed in the interior of the collection bag for removal from the body.

Some of the advantages of the present invention include improved visibility in endoscopic procedures, reduced need for insufflation, improved exposure of operative sites, protection of surrounding tissue and organ structure, irrigation and/or aspiration or drainage, cleansing of debris, stones, pus and other substances, such as fluids released by a ruptured appendix, bowel or cyst, allowing expansion of an absorbent material to greater sizes within the body, facilitating introduction and withdrawal of the devices through a narrow portal, reducing or preventing the undesirable release into the body of substances collected by the multifunctional devices, collecting substances within the body and miniaturizing the collected substances simultaneously and withdrawing collected substances from the body.

These and other objects, advantages and benefits are realized with the present invention as characterized in a multifunctional device for use in endoscopic procedures in the body including an elongate outer member, an elongate inner member and a loop forming portion connected between the outer member and the inner member for being introduced in the body. The loop forming portion is movable from a non-deployed position facilitating introduction in the body to a deployed position forming a loop configuration within the body for performing many various procedures. The loop configuration of the loop forming portion in the deployed position can be utilized to collect substances in the body, and the loop forming portion can be made of an absorbent material for absorbing substances in the body. The loop forming portion is movable, from externally of the body, to squeeze absorbed or collected substances from the loop forming portion.

A method of facilitating the performance of endoscopic operative procedures according to the present invention includes the steps of introducing the loop forming portion in the body in the non-deployed position, moving the loop forming portion from externally of the body to the deployed position, performing an operative procedure with the loop forming portion, moving the loop forming portion to the non-deployed position from externally of the body and withdrawing the loop forming portion from the body.

A collection system according to the present invention includes a collection bag for being introduced in the body and being movable, from externally of the body, from a non-expanded position facilitating introduction in the body to an expanded position in the body allowing substances to be introduced in the interior of the collection bag. A lumen coupled with the interior of the collection bag and connectable with a source of suction allows substances deposited in the interior of the collection bag to be withdrawn from the body.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a broken side view, partly in section, of a multifunctional device according to the present invention.

FIG. 2 is a broken, side sectional view of a distal portion of the multifunctional device of FIG. 1 in a non-expanded position.

FIG. 3 is a broken, side sectional view of the distal portion of the multifunctional device of FIG. 1 in an expanded position forming a loop configuration.

FIG. 4 is an end view of the distal portion of the multifunctional device of FIG. 1 in the expanded position.

FIG. 5 is a broken side view, partly in section, of the distal portion of the multifunctional device of FIG. 1 in a twisted state.

FIG. 6 is a broken side view of a collection system according to the present invention.

FIG. 7 is a broken, side sectional view of a distal portion of the collection bag assembly of the collection system of FIG. 6.

FIG. 8 is a broken, fragmentary side view of the inner member and collection bag of the collection bag assembly of FIG. 7.

FIG. 9 is a broken side view, partly in section, of the suction cutter assembly of the collection system of FIG. 6.

FIG. 10 is a broken, side sectional view of a distal portion of the collection system of FIG. 6 with the collection bag in an expanded position.

FIG. 12 is a broken side view of a modification of a multifunctional device according to the present invention.

FIG. 13 is a broken side view, partly in section, of a distal portion of the multifunctional device of FIG. 12 showing attachment of a strip to the inner and outer members of the multifunctional device.

FIG. 14 is a broken side view of the distal portion of the multifunctional device of FIG. 12 in the expanded position.

FIG. 15 is a broken perspective view of a strip and spine for the multifunctional device of FIG. 12.

FIG. 16 is a broken side view of the spine of FIG. 15.

FIG. 17 is a broken side view of the distal portion of the multifunctional device of FIG. 12 in an adjusted position.

FIG. 20 is a broken side view of the distal portion of another modification of a multifunctional device according to the present invention in an expanded position.

FIG. 21 illustrates the distal portion of FIG. 20 with some of the strips broken away.

FIG. 22 is a broken side view, partly in section, of the distal portion of a further modification of a multifunctional device according to the present invention in the expanded position.

FIG. 23 is a broken side view, partly in section, of the distal portion of an additional modification of a multifunctional device according to the present invention in the expanded position.

FIG. 24 is a broken side view, partly in section, of another modification of a multifunctional device according to the present invention in the expanded position with one of the strips detached to form a protruding probe.

FIG. 25 is a broken side view of a modification of a multifunctional device in combination with a suction cutter assembly according to the present invention.

FIG. 26 is a broken side view, partly in section, of the distal portion of a modification of a suction cutter assembly according to the present invention.

FIG. 27 is a broken, side sectional view of the distal portion of FIG. 26.

FIG. 28 is a broken side view, partly in section, of a modification of a handle assembly for use in the present invention.

DESCRIPTION OF THE PREFERRED EMBODIMENTS

Figure 11:
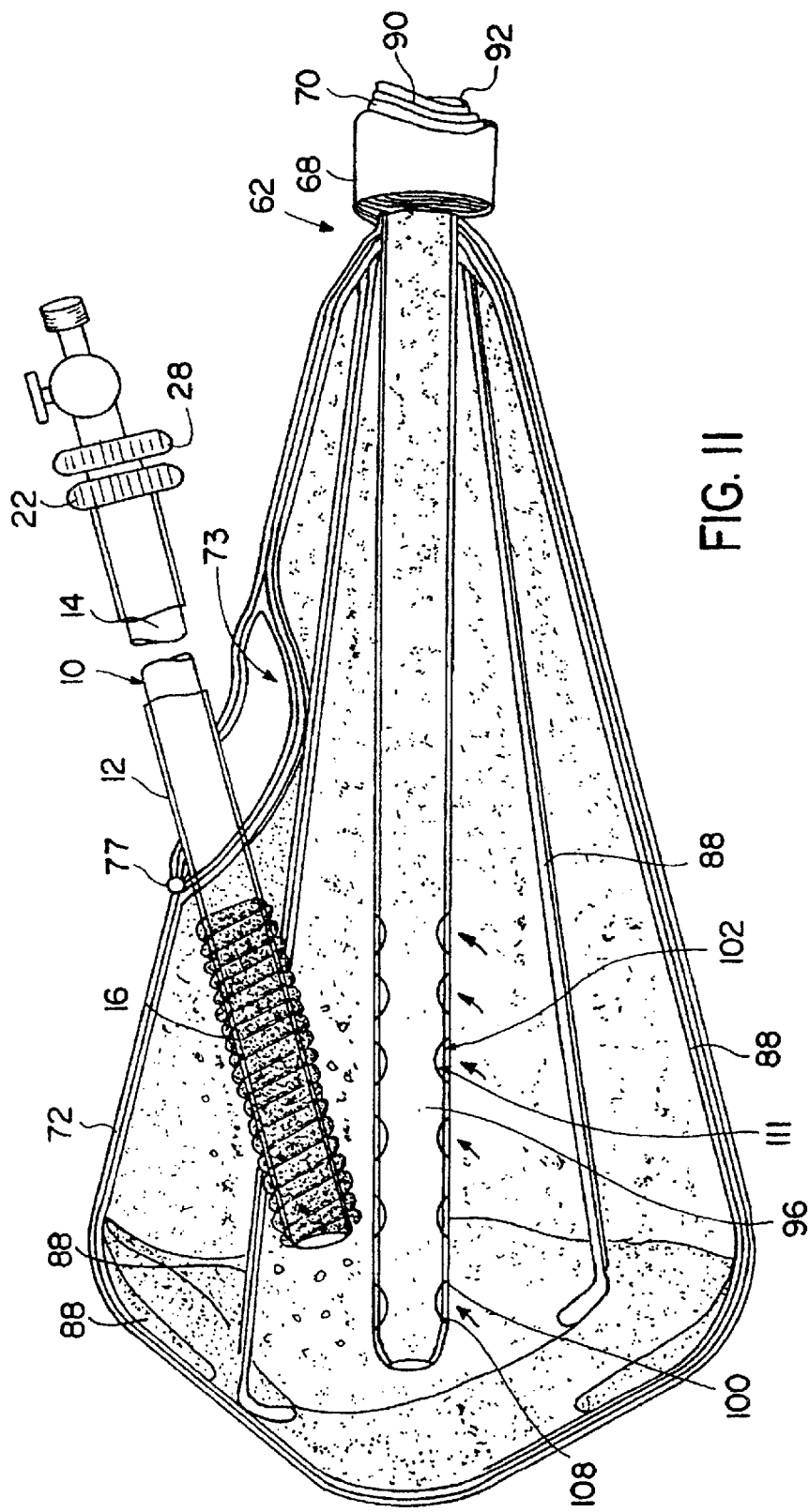
FIG. 11 is a broken perspective view illustrating use of the collection system in combination with a multifunctional device according to the present invention.

A multifunctional device 10 in accordance with the present invention is illustrated in FIG. 1 and includes an elongate outer member 12, an elongate inner member 14 disposed in outer member 12, a loop or mop forming portion 16 connected between the outer member 12 and the inner member 14 and a handle assembly 18 mounting the outer member 12 and the inner member 14. Outer member 12 terminates distally at a distal end 20 connected with loop forming portion 16 and proximally at a transverse flange 22 at a proximal end of the outer member mounted to handle assembly 18. Outer member 12 has an internal lumen or passage therethrough for receiving the inner member 14 with a close fit to minimize the cross-sectional size of the multifunctional device 10 to facilitate introduction through a narrow portal while permitting relative movement of one or both of the outer member 12 and the inner member 14. Outer member 12 can be made of any suitable rigid, semi-rigid, flexible or bendable medical grade material and can have any desirable size and configuration in cross-section, including tubular and non-tubular cross-sectional configurations, in accordance with procedural use.

Inner member 14 can be made of any suitable rigid, semi-rigid, flexible or bendable medical grade material and can have any desirable size and configuration in cross-section to be received in the lumen or passage of outer member 12. Inner member 14 terminates distally at a distal end 24 connected with loop forming portion 16 and proximally at a proximal end mounted to handle assembly 18. The inner member 14 carries or forms an actuating knob 26 and a transverse flange 28 disposed distally of actuating knob 26 for mounting the inner member 14 to the handle assembly 18 as explained further below. Inner member 14 includes an internal lumen or passage 29 therethrough allowing fluids and/or various medical instruments to be passed through device 10. One or both of the outer member 12 and the inner member 14 is mounted for movement in a first direction relative to the other of the outer member 12 and the inner member 14. In addition, one or both of the outer member 12 and the inner member 14 can be mounted for movement in a second direction, different than the first direction, relative to the other of the outer member 12 and the inner member 14. In the multifunctional device 10, both the outer member 12 and the inner member 14 are longitudinally movable distally and proximally relative to one another for movement in a first direction, and at least the inner member 14 is mounted for clockwise and/or counterclockwise rotational movement relative to the outer member 12 for movement in a second direction as accomplished via manual rotation of actuating knob 26. Actuating knob 26 can have any desirable configuration; and, preferably, actuating knob 26 is configured to be accessed and operated by the hand grasping handle assembly 18. As shown in FIG. 1, actuating knob 26 is in the nature of a circumferential transverse shoulder or ring having external ridges thereon to facilitate rotation by the surgeon's thumb.

Loop forming portion 16 includes one or more strips, strands or strings 30, each of which has a first end connected to the distal end 20 of outer member 12 and a second end connected to the distal end 24 of inner member 14. The loop forming portion 16 can be made of an absorbent material for absorbing substances such as fluids and/or bodily tissue, or the loop forming portion 16 can be made of a non-absorbent material including a resilient, flexible, stretchable, expandable or bendable membrane. As shown, the loop forming portion 16 for the multifunctional device 10 includes a plurality of strips 30 made of an absorbent material. The strips 30 can be made of an expandable material or a non-expandable material, and the strips 30 can be expandable in size upon absorption of fluids such that the cross-sectional size of the strips in a wet state upon absorbing fluids in the body is greater than the cross-sectional size of the strips in a dry state prior to absorbing fluids. The material selected for strips 30 can vary in accordance with the rigidity and configuration desired for loop forming portion 16 in a deployed position; and, accordingly, the strips 30 can be soft or floppy or somewhat hard and rigid. The strips 30 can be covered individually with a flexible, resilient, stretchable, expandable or bendable membrane or the loop forming portion 16 in whole or in part can be covered with or formed by a flexible, resilient, stretchable, expandable or bendable membrane. Strips 30 can be provided with various therapeutic substances, such as medicaments or coagulating agents, and such substances can be carried on the surfaces or within the material of the strips 30. The surfaces of strips 30 can be smooth or irregular or rough depending on procedural use.

Strips 30 for device 10 have their first ends attached to a circumferential peripheral edge of outer member 12 at the distal end 20 thereof at closely spaced locations about a longitudinal axis of outer member 12. The second ends of strips 30 are attached to a circumferential peripheral edge of inner member 14 at the distal end 24 thereof at closely spaced locations about a longitudinal axis of the inner member 14 corresponding to the locations along outer member 12. The strips 30 can be arranged on the outer and inner members in many various ways in accordance with the configuration desired for loop forming portion 16 in the deployed position, and the strips 30 can be attached to the outer and inner members at different, non-corresponding locations. The ends of strips 30 can be connected or attached to the outer and inner members in many various ways including adhesively or via retention of the ends of strips 30 in recesses in the walls of the outer and inner members as shown in FIG. 13.

Some or all of the strips 30 can be designed to assume a predetermined configuration in the deployed position. The strips 30 can be designed in many various ways to have a predetermined configuration in the deployed position. For example, strips 30 can be made of a material having a shape memory or a spine can be provided for guiding the strips 30 to the predetermined configuration. Examples of various spine members suitable for use in the present invention are disclosed in applicant's prior applications incorporated herein by reference. Where a spine is utilized, the spine can be hollow, tubular or provided with an internal passage for aspiration and/or delivery of substances, such as medicaments, to and from the body via the spine.

Handle assembly 18 includes a generally U-shaped handle having a distal handle arm 32 and a proximal handle arm 34 connected by a curved spring segment 36. The handle arms 32 and 34 and the spring segment 36 can be made as separate components pivotally connected to one another, or the handle arms 32 and 34 and the spring segment 36 can be made integrally, unitarily as shown in FIG. 1. Distal handle arm 32 carries a collar 38 having a recess therein for mounting the outer member proximal flange 22. Proximal handle arm 34 carries a collar 40 having a recess therein for mounting the transverse flange 28 of the inner member 14 with the inner member 14 passing through aligned openings in the collars 38 and 40. The handle assembly 18 can be designed to be permanently connected to the outer member 12 and the inner member 14, or the handle assembly 18 can be designed to be removable or detachable from the outer member 12 and the inner member 14. Relative displacement of the handle arts 32 and 34 via squeezing thereof causes relative longitudinal movement of outer member 12 and inner member 14, and a locking mechanism 42 can be provided in handle assembly 18 to fix the relative position of the handle arms 32 and 34.

Locking mechanism 42 includes a locking bar 44 pivotally mounted at one end to proximal handle arm 34 by a hinge, pivot or joint 46. The locking bar 44 extends through a slot 48 in distal handle arm 32 to terminate at a downwardly angled operating lever 50, and the locking bar 44 is rotationally biased toward an upper end of slot 48 by a torsion spring (not shown) at joint 46. A plurality of locking teeth 52 are disposed on an upper surface of locking bar 44 along the length thereof for cooperative engagement with locking teeth 54 formed in distal handle arm 32 along an upper wall of slot 48. Locking teeth 52 are angled proximally to permit movement of handle arms 32 and 34 toward one another in response to squeezing operation of handle assembly 18, and locking teeth 54 are configured to prevent movement of handle arms 32 and 34 away from one another upon termination of the squeezing force.

An inlet assembly 56 is coupled or formed with the inner member 14 and includes a hollow member, such as tube 58, coupled with the lumen 29 of inner member 14 and a valve 60 for opening and closing the lumen 29 of the inner member 14 to allow fluid flow and/or instruments to be passed therethrough when the valve 60 is open and to close off or seal the lumen 29 when the valve 60 is closed. Valve 60 can have any desirable construction; and, as shown in FIG. 1, valve 60 includes a ball-cock valve along tube 58. The inlet assembly 56 can be formed separately from inner member 14 in which case tube 58 can extend into the lumen 29 of inner member 14, or the inlet assembly 56 can be formed integrally, unitarily with inner member 14 in which case tube 58 can be formed as an extension of the inner member 14 as shown for device 10. Where the inlet assembly 56 is formed separately from the inner member 14, the inlet assembly 56 can be coupled to inner member 14 in many various ways to prevent rotation of inlet assembly 56 when the inner member 14 is rotated relative to the outer member 12, or the inlet assembly 56 can be allowed to rotate with the inner member 14.

The multifunctional device 10 is normally supplied as shown in FIG. 1 with handle arms 32 and 34 biased away from one another by spring segment 36 to position the distal end 20 of outer member 12 and the distal end 24 of inner member 14 such that the loop forming portion 16 is in a non-deployed position. As shown for the multifunctional device 10, the handle assembly 18 is designed to normally position the inner member distal end 24 proximally of the outer member distal end 20 a distance substantially corresponding to the length of strips 30. Accordingly, loop forming portion 16 is biased to the non-deployed position with strips 30 in a substantially straight or straight configuration extending lengthwise or longitudinally within outer member 12 between the outer member distal end 20 and the inner member distal end 24 parallel or substantially parallel with a longitudinal axis of multifunctional device 10. Therefore, a distal portion of the multi-functional device 10 has a substantially uniform cross-section in the non-deployed position facilitating introduction in the body through a narrow portal.

When it is desired to utilize the multifunctional device 10 in endoscopic operative procedures, the distal portion of the multifunctional device 10 in the non-deployed position is introduced in the body through a relatively narrow portal, which can include a structural channel such as a portal sleeve or cannula, an incisional opening or a natural entry opening providing access through an anatomical wall, such as an anatomical cavity wall W as shown in FIG. 2 wherein the device 10 is introduced through a portal sleeve S. In the non-deployed position, handle arms 32 and 34 will be held in place by locking bar 44 preventing relative longitudinal movement of outer member 12 and inner member 14, and the cross-sectional size of the distal portion of multifunctional device 10 will be substantially uniform to facilitate introduction through the narrow portal. Once the distal portion of the multifunctional device 10 is positioned in the body, such as in the anatomical cavity or in tissue within or forming the anatomical cavity, handle arms 32 and 34 disposed externally of the body are manually squeezed causing the handle arms 32 and 34 to be moved toward one another against the bias of spring segment 36 as permitted by the proximal angle of teeth 52 and the torsion spring at joint 46. Movement of handle arms 32 and 34 via squeezing operation of handle assembly 18 causes outer member 12 and inner member 14 to move longitudinally relative to one another. Accordingly, the outer member distal end 20 and the inner member distal end 24 will be moved toward one another causing the loop forming portion 16 to be moved to the deployed position illustrated in FIGS. 3 and 4. Movement of handle arms 32 and 34 is controlled via locking teeth 52 and 54 with cooperative engagement of the locking teeth 52 and 54 maintaining the handle arms 32 and 34 and, therefore, the outer member 12 and inner member 14, in a desired position upon termination of the squeezing force on the handle assembly 18.

In the deployed position, strips 30 are folded or bent to form a loop or mop configuration at the distal portion of multifunctional device 10. As shown in FIGS. 3 and 4, loop forming portion 16 forms a multiple loop configuration with strips 30 protruding distally beyond the outer member distal end 20 and curving or bending inwardly to extend proximally to the inner member distal end 24 which remains within the outer member 12. The loops formed by strips 30 in the deployed position are disposed about the longitudinal axis of the multifunctional device 10 allowing fluid flow and/or instruments to be introduced in the body through the inlet assembly 56 and the lumen 29 of inner member 14. In the deployed position, the multiple loop or mop structure defined by loop forming portion 16 can be used to perform various functions including creating or increasing the size of a space within the body, absorption of substances such as fluids and tissue by the material of strips 30 or collection of substances within the recesses formed by the loops, cleansing of debris, stones, pus and other materials, such as materials released by a ruptured capsule or organ including a ruptured cyst, appendix or bowel, manipulating or retracting tissue or organ structures, separating adhering tissue, dissecting tissue, isolating tissue to be treated, protecting surrounding tissue and increasing visibility for the surgeon.

The loop forming portion 16 has a predetermined configuration in the deployed position forming an enlargement or protrusion at the distal portion of device 10 having a cross-sectional size greater than the cross-sectional size of the distal portion of device 10 prior to deployment of the loop forming portion 16. As shown for multifunctional device 10, the enlargement formed by loop forming portion 16 protrudes outwardly in a direction transverse to the longitudinal axis of the multifunctional device 10. The size and configuration of the loop forming portion 16 can be changed or varied during use by selectively extending and/or retracting the loop forming portion 16 via operation of handle assembly 18. When it is desired to retract loop forming portion 16 further into outer member 12 in a partially deployed position or to move loop forming portion 16 to the non-deployed position, operating lever 50 is grasped, preferably by a finger of the hand grasping the handle assembly 18, and is moved downwardly against the upward rotational bias of the torsion spring at joint 46 to disengage teeth 52 from teeth 54. With the locking teeth 52 and 54 disengaged, spring segment 36 will urge handle arms 32 and 34 away from one another causing relative movement of the outer and inner members to move loop forming portion 16 toward the non-deployed position. The lever 50 can be released at any time to reengage teeth 52 with teeth 54 thusly fixing the position of handle arms 32 and 34 and, therefore, loop forming portion 16. Upon return of the loop forming portion 16 to the non-deployed position, the multifunctional device 10 can be withdrawn from the body through the narrow portal.

Prior to withdrawal of the multifunctional device 10 from the body, fluids and/or tissue absorbed or collected by loop forming portion 16 can be removed therefrom by manually rotating the actuating knob 26 causing the inner member 14 to be rotated relative to the outer member 12. Rotation of inner member 14 relative to outer member 12 causes the strips 30 to be twisted in a wringing action to assume a twisted state thusly squeezing fluids and/or other materials from the loop forming portion 16 as shown in FIG. 5. The loop forming portion 16 can be twisted or wrung when in the non-deployed position or when in the deployed position as shown in FIG. 5. Where it is undesired for the fluids or tissue wrung from loop forming portion 16 to be released into the body, the multifunctional device 10 can be utilized with a collection system as described further below, or the inner member distal portion can be provided with holes as illustrated in FIG. 21 for withdrawal of the fluids or tissue through lumen 29 when suction is applied via inlet assembly 56. Squeezing or wringing to remove absorbed or collected substances allows the loop forming portion 16 to be reused during the course of the procedure being performed for further absorption and/or collection and permits the size of the loop forming portion to be reduced facilitating return to the non-deployed position and/or withdrawal from the body through the narrow portal.

The outer member 12, the inner member 14 and the handle assembly 18 can be designed in many various ways to normally position the outer member distal end 20 and the inner member distal end 24 in accordance with the structure of the loop forming portion 16 such that the distal portion of the device 10 has a substantially uniform cross-section in the non-deployed position to facilitate introduction in the body through a narrow portal. The arrangement of strips 30 in the non-deployed position can vary depending on the initial position of the outer and inner members and/or the configuration of strips 30 and the manner in which the strips 30 are attached to the outer and inner members. Various handle assemblies can be utilized with the multifunctional devices of the present invention to effect relative longitudinal and rotational movement of the outer member and/or the inner member, and the multifunctional devices can be formed of two or more elongate members. One or both of the outer member and the inner member can be mounted for rotation; and, as shown in FIG. 1, the outer member proximal flange 22 can form or be connected with an actuating knob 23 disposed externally of collar 38 for rotating the outer member 12 relative to the inner member 14 as guided by the recess of collar 38.

The multifunctional devices according to the present invention can be utilized in endoscopic procedures in many various areas of the body including abdominal, joint, orthopedic, gastrointestinal, spinal, bone, sinus, vascular, uterine and gall bladder cavities, for example. The multifunctional devices according to the present invention are particularly useful to create a space from a non-existing space or from a potential space in the body or to create or increase the size of any area or space in the body to carry out endoscopic diagnostic and/or therapeutic procedures. Various devices can be introduced in the body through the lumen of the inner member including suction cutting instruments, suture needles, needle holders, clips and clip appliers, ring and string applicators, sponge sticks, dissecting probes, scissors, biopsy forceps, and holding or grasping instruments. Various substances, including medicaments, irrigating fluids and bodily fluids, can be introduced in and withdrawn from the body via the multifunctional devices. The outer member and/or inner member can be provided with various adjustment systems or controls, such as wires, for adjusting or changing the direction or orientation of the loop forming portion within the body.

FIG. 6 illustrates at 62 a collection system particularly useful with the multifunctional devices of the present invention to collect fluids and/or other materials, such as solid materials, released from the loop forming portion prior to withdrawal of the multifunctional devices from the body. The collection system 62 includes a collection bag assembly 64 and a suction cutter assembly 66. As shown in FIGS. 6 and 7, collection bag assembly 64 includes an elongate outer member 68, an elongate inner member 70 disposed in outer member 68 and a collection bag 72. Outer member 68 terminates distally at a distal end 76 and proximally at an enlarged, transverse flange or shoulder 78. Outer member 68 includes an internal lumen or passage therethrough for receiving the inner member 70 with a close fit to minimize the cross-sectional size of the collection system for introduction through a narrow portal while permitting relative longitudinal movement of one or both of the outer member 68 and the inner member 70. The outer member 68 can be made of any suitable rigid, semi-rigid, flexible or bendable medical grade material and can have any desirable size and configuration in cross-section, including tubular and non-tubular cross-sectional configurations, to be introduced in the body through the narrow portal. Inner member 70 can be made of any suitable rigid, semi-rigid, flexible or bendable medical grade material and can have any desirable size and configuration in cross-section to be received in the lumen or passage of outer member 68. Inner member 70 terminates distally at a distal end 80 and proximally at an enlarged, transverse flange or shoulder 82. The inner member 70 has an internal lumen or passage therethrough for receiving a suction cutter of the suction cutter assembly 66 as explained further below.

Collection bag 72 is arranged in the assembly 64 to be movable between an expanded position and a non-expanded or collapsed position in response to longitudinal movement of outer member 68 and/or inner member 70. Collection bag 72 for assembly 64 is carried by the inner member 70 and includes a single layer or multiple layers of material configured to have a forward or distal end and a rearward or proximal end attached to inner member 70. Collection bag 72 can be made of any desirable medical grade material, such as fluid-proof plastic, to be movable or collapsible from the expanded position as shown in FIG. 7 to the non-expanded or collapsed position wherein the collection bag 72 is disposed within the outer member 68 as shown in FIG. 6. The collection bag 72 can be attached to the inner member 70 in many various ways, such as adhesively or mechanically including the use of various bonds or seals. As shown in FIG. 8, bag 72 includes a rearward or proximal edge 84 received within a circumferential recess 86 at the distal end 80 of the inner member 70 with the recess 86 being disposed within the thickness of the wall forming the inner member 70. Accordingly, when attached to inner member 70, bag 72 defines an enclosed or substantially enclosed space or interior communicating with the internal passage or lumen of the inner member 70. Bag 72 includes an access slot or opening 73 in a side wall thereof communicating with the interior of bag 72 and with the lumen of inner member 70. The access slot or opening 73 can be provided with a slide closure or zipper 75 operable by an operating tab 77 to selectively close the opening 73 as shown in dotted lines in FIG. 7 and to selectively open the opening 73 to permit positioning of loop forming portion 16 in bag 72. Bag 72 can have various sizes and configurations in the expanded position in accordance with procedural use, and the bag 72 can be biased toward the expanded position. The bag 72 can be biased toward the expanded position in many various ways, such as by forming the bag of a material having a shape memory or with the use of a mechanical, shape-retaining reinforcement or a spine.

FIG. 7 illustrates a spine 74 for moving collection bag 72 to the expanded position and for permitting the collection bag 72 to be moved to the non-expanded or collapsed position. Spine 74 is carried by the inner member 70 and includes a plurality of arms 88 attached to the distal end 80 of inner member 70 at spaced locations about a longitudinal axis of the inner member 70. The spine 74 includes four arms 88 attached to the inner member 70 at 90° spaced locations about the inner member longitudinal axis, only three arms 88 being visible in FIG. 7. Arms 88 extend distally from the inner member 70 and are biased in a direction outwardly of or transverse to a longitudinal axis of the inner member to be normally disposed in an expanded position as shown in FIG. 7. Spine 74 can be biased in many various ways to be normally disposed in the expanded position and to be movable to a non-expanded or collapsed position by outer member 68 when the spine 74 is disposed in the outer member 68.

Outer member 68 and inner member 70 are longitudinally movable relative to one another by squeezing operation of flanges 78 and 82 to move spine 74 and, therefore, bag 72, from the non-expanded position wherein bag 72 and spine 74 are disposed in outer member 68 to the expanded position wherein bag 72 and spine 74 are disposed distally of outer member 68. A locking mechanism can be provided for fixing the relative positions of flanges 78 and 82 and, as shown in FIG. 6, includes a locking bar 131 pivotally mounted at one end to flange 82 by a joint, pivot or hinge 133. The locking bar 131 is rotationally biased toward flange 78, i.e., clockwise looking at FIG. 6, by a torsion spring (not shown) at joint 133. A plurality of locking teeth 135 are disposed on an upper surface of locking bar 131 along the length thereof for cooperative engagement with ridges 137 on flange 78. Locking teeth 135 are angled proximally to permit movement of flanges 78 and 82 toward one another in response to squeezing operation thereof, and ridges 137 are configured to prevent movement of flanges 78 and 82 away from one another upon termination of the squeezing force. The end of locking arm 131 opposite joint 133 terminates at an angled operating lever 139 for disengaging teeth 135 from ridges 137 to permit movement of flanges 78 and 82 away from one another. Where it is desired for the collection bag 72 to be biased to the collapsed position within outer member 68, various springs or other bias devices can be provided between flanges 78 and 82 to bias the outer member 68 distally and/or the inner member 70 proximally.

Suction cutter assembly 66 is best illustrated in FIG. 9 and includes a suction cutter having an elongate outer member 90, an elongate inner member 92 disposed within outer member 90 and a handle assembly 94 mounting the outer member 90 and inner member 92. Outer member 90 can be made of any suitable medical grade material having sufficient rigidity and strength for cutting anatomical tissue and terminates distally at a distal portion 96, a part of which is broken away in FIG. 9, and proximally at a proximal end 98 mounted to handle assembly 94. Outer member 90 can have various cross-sectional configurations and sizes, including a tubular configuration as shown, to be received within the lumen of the inner member 70 of collection bag assembly 64 and includes a lumen or internal passage for receiving inner member 92. A cutting edge 100 is defined on the distal portion 96 for cutting anatomical tissue in cooperation with a cutting edge on the inner member 92. The cutting edge 100 can have various configurations to cooperate with the cutting edge on the inner member 92; and, as shown, cutting edge 100 includes a plurality of longitudinally aligned circular cutting edges 100 defined along wall surfaces of the outer member 90 circumscribing apertures 102 in the wall of the outer member 90 communicating with the lumen or internal passage thereof.

Inner member 92 can be made of any suitable medical grade material with sufficient rigidity and strength to cut anatomical tissue and terminates distally at a distal portion 104, a part of which is broken away in FIG. 9, and proximally at a proximal end 106 mounted to handle assembly 94. The inner member 92 can have various cross-sectional configurations and sizes to cooperate with outer member 90 and to be received in the lumen of the outer member with a close fit while permitting relative longitudinal and/or rotational movement of one or both of the outer member 90 and the inner member 92. The inner member 92 includes a lumen or internal passage 93 therethrough allowing flow of fluids and other materials through the suction cutter, and a cutting edge 108 is defined on the distal portion 104 for cooperating with the cutting edge 100 on outer member 90. As shown, the cutting edge 108 includes a plurality of longitudinally aligned circular cutting edges 108 defined along wall surfaces of the inner member 92 circumscribing apertures 111 in the wall of the inner member 92 communicating with the lumen 93. Cutting edge 108 is designed to cooperate with cutting edge 100 to cut anatomical tissue via relative rotation of one or both of the cutting edges 100 and 108 and/or relative longitudinal movement of one or both of the cutting edges 100 and 108.

Handle assembly 94 mounts the outer member 90 and the inner member 92 to normally position the apertures 102 and 111 and, therefore, the cutting edges 100 and 108 in alignment to form a scalloped cutting edge as shown in FIG. 9. The handle assembly 94 can incorporate various structure or components to permit manual and/or electrically powered longitudinal and/or rotational movement of one or both of the outer member 90 and the inner member 92. The handle assembly 94 for suction cutter assembly 66 is manually operated and includes a generally U-shaped handle, similar to the handle of handle assembly 18, having a distal handle arm 113 and a proximal handle arm 115 connected by a curved spring segment 117. Distal handle arm 113 carries a collar 119 secured to the proximal end 98 of the outer member 90. The proximal handle arm 115 carries a collar 121 having a recess therein for mounting a transverse flange 141 on the inner member 92 with the inner member 92 passing through aligned openings in the collars 119 and 121. The inner member 92 is coupled with or forms an inlet assembly 125 including a tube coupled with the lumen 93 of the inner member 92 and a valve 127 for opening and closing the lumen 93 to allow fluid flow and/or instruments to be passed therethrough when the valve is open and to close off or seal the lumen 93 when the valve 127 is closed. The inlet assembly 125 is similar to inlet assembly 56 and can be formed integrally with the inner member 92 as shown in FIG. 9 or separately therefrom. The outer member 90 and inner member 92 are movable longitudinally relative to one another via manual squeezing operation of handle arms 113 and 115; and, additionally, the inner member 92 is manually rotatable within the outer member 90 via rotation of an actuating knob 143 on inlet assembly 125.

When it is desired to utilize the collection system 62, the suction cutter assembly 66 is assembled with the collection bag assembly 64 as shown in FIG. 6 with the bag 72 in the non-expanded position. Accordingly, flanges 78 and 82 are spaced from one another to position the inner member distal end 80 proximally of the outer member distal end 76 such that bag 72 and spine 74 are disposed within the outer member 68 with the flanges 78 and 82 held in place by locking bar 131. In the non-expanded position, spine 74 is collapsed within outer member 68 with arms 88 disposed parallel or substantially parallel with one another and with a longitudinal axis of the collection bag assembly 64, and bag 72 is collapsed around spine 74. To assemble the suction cutter assembly 66 with the collection bag assembly 64, the outer member 90 of the suction cutter is disposed in the lumen of the inner member 70 of the collection bag assembly 64. With a forward end of collar 119 in abutment with flange 82, the scalloped cutting edge formed by the aligned cutting edges 100 and 108 will be disposed within the collection bag 72 with the cutting edges 100 and 108 being maintained in alignment by handle arms 113 and 115 as positioned by spring segment 117. If desired, the collection bag assembly 64 can be removably secured to the suction cutter assembly 66, such as by a pivotable or rotatable detent or clamp 145 for removably locking the flange 82 to the collar 119. The arms 88 of spine 74 and the collection bag 72 will be collapsed about the distal portion 96 of the suction cutter assembly, and the collection system 62 will be ready for use with the outer member 68 providing a smooth, uniform profile for introduction in the body through a narrow portal.

When the collection system 62 is utilized in combination with the multifunctional devices of the present invention, such as multifunctional device 10, the distal end of outer member 68 is introduced in the body through a narrow portal, which can be a structural channel, an incisional opening or a natural entry. Once the outer member distal end is properly positioned in the body, the flanges 78 and 82 are manually grasped and squeezed toward one another causing the outer member 68 and the inner member 70 to move longitudinally relative to one another as permitted by teeth 135 and the spring at joint 133. Longitudinal movement of outer member 68 and inner member 70 toward one another causes the collection bag 72 and spine 74 to be extended beyond the distal end 76 of the outer member 68. Extension of collection bag 72 and spine 74 beyond the outer member distal end 76 causes spine 74 to automatically move to the expanded position thusly moving bag 72 to the expanded position. Spine 74 will maintain the expanded configuration for bag 72, and the distal portion 96 of the suction cutter will be disposed within the thusly expanded bag 72 as shown in FIG. 10.

The multifunctional device 10 is manipulated from externally of the body to position the loop forming portion 16 within the collection bag 72 through the opening 73 as shown in FIG. 11. Once the loop forming portion 16 has been positioned in the collection bag 72, the outer member 12 and/or the inner member 14 are rotated relative to one another, such as via flanges 22 and 28, it being noted that the multifunctional device in FIG. 11 does not have a U-shaped handle. Rotation of outer member 12 and inner member 14 wrings or twists the loop forming portion 16 thusly squeezing fluids and/or tissue therefrom and into bag 72. Accordingly, substances absorbed and/or collected by the loop forming portion 16 will be released into the collection bag 72 and not into the body. When the inlet assembly 125 of the suction cutter assembly 66 is coupled with a source of suction or vacuum, substances released into the collection bag 72 will be drawn through the aligned apertures 102 and 111 and into the lumen 93 of the inner member 92 for withdrawal from the body. Solid materials drawn through apertures 102 and 111 can be cut or miniaturized via movement of one or both of the cutting edges 100 and 108 past one another. In the collection system 62, actuation of the cutting function is accomplished by either squeezing handle arms 113 and 115 causing relative longitudinal movement of outer member 90 and inner member 92 with concomitant longitudinal movement of cutting edges 100 and 108 past one another or rotating knob 125 causing rotation of inner member 92 relative to outer member 90 with concomitant rotational movement of cutting edge 108 past cutting edge 100 to cut tissue or other materials positioned in or drawn into apertures 102.

Once substances have been removed from the loop forming portion 16, the loop forming portion 16 can be withdrawn from bag 72, and the tab 77 can be utilized to close the access slot or;and opening 73 of the bag to prevent release of collected substances into the body. It should be appreciated that various instruments, such as grasping forceps, can be utilized to grasp and to operate the tab 77. When it is desired to withdraw the collection system from the body, operating lever 139 is grasped and rotated, i.e., counterclockwise looking at FIG. 6, to disengage teeth 135 from ridges 137 allowing flanges 78 and 82 to be manually moved away from one another. Movement of flanges 78 and 82 away from one another causes relative longitudinal movement of outer member 68 and inner member 70 to position bag 72 and spine 74 in outer member 68 thusly causing the bag 72 to be moved to the non-expanded position. Accordingly, the outer member 68 presents a uniform profile facilitating withdrawal from the body through the narrow portal.

It will be appreciated that the collection bag assembly and the suction cutter assembly can be built as separate assemblies or as a single unit. The suction cutter can be insertable in the collection bag, permanently or removably attached or partially attached to the collection bag or partly within and/or partly exposed from the collection bag to access various anatomical body cavities and/or structures. The collection bag can be attached to the suction cutter in many various ways including attachment to a wall of the suction cutter. In the non-expanded position, the bag can be wrapped around the suction cutter. The collection bag assembly and the suction cutter assembly can include any number of elongate members. Various spines can be utilized in the collection bag assembly including various forceps and tongs. The spines can be attached to the bag, to the inner member or to some other component of the bag assembly. The bag can have various sizes and configurations including conical, oval and toroidal or donut-shaped configurations. The collection bag can have various openings, including oblique openings, and the openings can be provided in the side wall of the collection bag or at the forward and/or rearward ends of the collection bag. Suction through the suction cutter can be controlled via alignment and non-alignment of the suction cutter apertures, and cutting can be accomplished manually or with assisted power, such as electrically. Suction can be established through the inner member of the suction cutter or between the outer member and the inner member. The distal portion of the suction cutter can be covered by an absorbent material, which can be expandable or non-expandable.

The collection system according to the present invention provides a single instrument for performing the dual functions of collecting fluid and/or tissue and miniaturizing the collected tissue, and the collection system allows these functions to be performed via a single puncture procedure. The collection system allows increased quantities of undesirable fluids and other materials to be evacuated from the body without requiring replacement of the collection bag. Large size tissue specimens, such as tumors, can be placed in the collection bag within the body for miniaturization. The collection system facilitates removal from the body of various fluids as well as large size solids through a narrow portal without the need for additional instruments. The collection system enhances visualization in the endoscopic procedure being performed and permits immediate collection of specimens and fluids. The collection system can be utilized in various space creating procedures as well as the removal of lesions by cutting and suction. The collection system can be utilized with various other instruments suitable for releasing or depositing into the collection bag various substances to be removed from the body.

A modification of a multifunctional device according to the present invention is illustrated in FIG. 12 at 210. The multifunctional device 210 is similar to the multifunctional device 10, the primary differences between multifunctional device 210 and multifunctional device 10 being that loop forming portion 216 for multifunctional device 210 is not disposed in the outer member 212 in the non-deployed position, and the handle assembly 218 for multifunctional device 210 does not include a U-shaped handle structure. Loop forming portion 216 includes strips 230 having first ends connected to the distal end 220 of outer member 212 and second ends connected to the distal end 224 of inner member 214. FIG. 13 illustrates one way of connecting the strips 230 to the outer member 212 and the inner member 214. As shown in FIG. 13, each of the strips 230 has protruding tabs or fingers 247 at the first and second ends thereof for being received in slots 249 at the distal ends of the outer member 212 and the inner member 214. Slots 249 are open along the circumferential distal edges of the outer member 212 and the inner member 214, respectively, and extend into the thickness of the walls forming the outer and inner members.

Handle assembly 218 for multifunctional device 210 includes a transverse flange 222 at a proximal end of outer member 212, a transverse flange 228 coupled with inner member 214 and a locking mechanism 242 for fixing the relative position of flanges 222 and 228. The outer member flange 222 is disposed proximally of the inner member flange 228 which is coupled to the inner member 214 via a pin (not shown) secured to flange 228 and to inner member 214 with the pin extending through a longitudinal slot 251 in the outer member 212. Slot 251 is disposed parallel with a longitudinal axis of the multifunctional device 210 to permit longitudinal movement of the outer member 212 and/or the inner member 214 relative to one another in response to squeezing operation of flanges 222 and 228.

Locking mechanism 242 is similar to the locking mechanism for collection assembly 62 and includes a locking bar 231 pivotally mounted at one end to flange 222 by a joint, pivot or hinge 233. The locking bar 231 is rotationally biased toward flange 228, i.e., clockwise looking at FIG. 12, by a torsion spring (not shown) at joint 233. A plurality of locking teeth 235 are disposed on an upper surface of locking bar 231 along the length thereof for cooperative engagement with ridges 237 on flange 228. Locking teeth 235 are angled proximally to permit movement of flanges 222 and 228 toward one another in response to squeezing operation thereof, and ridges 237 are configured to prevent movement of flanges 222 and 228 away from one another upon termination of the squeezing force. The end of locking arm 231 opposite joint 233 terminates at an angled operating lever 239 for disengaging teeth 235 from ridges 237 to permit movement of flanges 222 and 228 away from one another.

Inlet assembly 256 for multifunctional device 210 can be coupled with outer member 212 or inner member 214 or can be formed as an extension of the outer member 212 or the inner member 214. As shown in. FIG. 12, the inlet assembly 256 includes a tube 258 coupled with or formed as part of the inner member 214 extending proximally of the outer member flange 222. Tube 258 includes a valve 260 for selectively opening and closing the lumen of inner member 214.

Prior to introduction in the body, flanges 222 and 228 are positioned as shown in FIG. 12 such that the distal end 220 of outer member 212 is disposed proximally of the distal end 224 of inner member 214 a distance corresponding to the length of strips 230. At this time, loop forming portion 216 will be in the non-deployed position with strips 230 extending lengthwise between the distal ends 220 and 224 parallel or substantially parallel with one another and with a longitudinal axis of the multifunctional device 210. Accordingly, the loop forming portion 216 in the non-deployed position forms a uniform profile along a distal portion of the multifunctional device 210 to facilitate introduction through a narrow portal.

Use of multifunctional device 210 in endoscopic procedures to perform various functions in the body is similar to that previously described in that the distal portion of the multifunctional device 210 is introduced in the body through a narrow portal; and, in the case of multifunctional device 210, it is advantageous for the device to be introduced in the body through a portal sleeve or cannula or to provide the multifunctional device 210 within an outermost member or sleeve which can form part of the device 210 or be separate therefrom. FIG. 12 illustrates in dotted lines an outermost elongate member 212' formed as part of multifunctional device 210 and having an internal lumen or passage for receiving outer member 212 and terminating proximally at a transverse flange 222' for moving the outermost member 212' longitudinally relative to the outer member 212 to selectively cover and expose the loop forming portion 216. Accordingly, the multifunctional device 210 can include three, or more, elongate members, and the loop forming portion can be disposed in a protected condition within outermost member 212' during introduction in the body through a portal.

Once the loop forming portion 216 is positioned in the body as desired, flanges 222 and 228 are squeezed with one hand causing the flanges 222 and 228 to be moved toward one another as permitted by locking teeth 235 and the torsion spring at joint 233. If the multifunctional device is provided with outermost member 212', the flange 222' is moved proximally to retract outermost member 212' and expose loop forming portion 216 prior to operation of handle assembly 218. Movement of flanges 222 and 228 toward one another causes concomitant longitudinal movement of outer member 212 and inner member 214. Accordingly, the outer member distal end 220 and the inner member distal end 224 will be moved toward one another causing the loop forming portion 216 to be moved to the deployed position illustrated in FIG. 14. Movement of flanges 222 and 228 is controlled via locking teeth 235 and ridges 237 maintaining the flanges 222 and 228 and, therefore, the outer member 212 and inner member 214, in a desired position upon termination of the squeezing force on the flanges 222 and 228. When it is desired to extend loop forming portion 216 further from the outer member 212 or to move loop forming portion 216 to the non-deployed position, operating lever 239 is grasped and is used to rotate the locking bar 231 downwardly, i.e. counterclockwise looking at FIG. 12, against the upward rotational bias of the torsion spring at joint 233 to disengage teeth 235 from ridges 237. With the teeth 235 and ridges 237 disengaged, flanges 222 and 228 can be moved away from one another causing relative movement of the outer and inner members to move loop forming portion 216 toward the non-deployed position or further toward one another to change the size and configuration of loop forming portion 216 in the deployed position.

In the deployed position illustrated in FIG. 14, each of the strips 230 has a predetermined configuration, and a spine 253 for guiding the strips 230 to assume the predetermined configuration is shown in FIGS. 15 and 16. FIG. 15 illustrates the predetermined configuration for strips 230 in the deployed position, only one strip 230 being shown. In the deployed position, strip 230 assumes a U-shape configuration and is bent back over itself at a 180° bend with opposite ends of the strip 230 extending lengthwise from the bend in the same direction. The strip 230 has substantially planar upper and lower surfaces 255 and 257 with a thickness therebetween and a width in a direction transverse to a longitudinal axis of the strip 230 that is substantially greater than the thickness for increased absorption capability. Spine 253 guides strips 230 to assume the predetermined configuration and, as best shown in FIG. 16, includes a length of material having shape memory to be normally disposed in the U-shape configuration. Spine 253 can have various cross-sectional configurations and sizes; and, as shown in FIG. 16, the spine 253 has a tubular cross-sectional configuration with a minimal outer diameter or size. Where the spine 253 is tubular or hollow, one or more apertures or holes 259 can be provided in the spine 253 to permit fluid flow to and from the body through the spine 253. Spine 253 can be arranged on or in the strip 230 in many various ways; and, as shown in FIG. 15, spine 253 is attached to the lower surface 257 of the strip 230. Spine 253 is arranged centrally along the width of strip 230 and extends along the length thereof, and the ends of spine 253 can be attached to the distal ends of the outer member 212 and the inner member 214, or the spine 253 can extend through the outer or inner member. Spine 253 is capable of being unbent or straightened in response to relative movement of the outer member 212 and the inner member 214 allowing strip 230 to be moved to the non-deployed position. Upon movement of flanges 228 and 222 to deploy loop forming portion 216, the shape memory of spine 253 causes it to return to the normal configuration thusly guiding strip 230 to the predetermined configuration corresponding to the normal configuration for spine 253. The spine 253 can be somewhat flexible to flex or give during use, or the spine 253 can be rigid. Where the spine extends through the device 210, the spine can be coupled with an inlet assembly to supply suction or fluid flow therethrough. Where the spine does not extend through the device 210, a passage can be formed through the wall of the outer or inner members communicating with the lumen of the spine, as shown in FIG. 24, and a supplemental conduit can be coupled with the passage for fluid flow through the spine.

In the multifunctional devices according to the present invention, the direction or orientation of the loop forming portions within the body can be adjusted or controlled during use. One way of allowing directional adjustment of the loop forming portions in the body is to form one or more of the elongate members with a segment capable of assuming a predetermined angle, bend or direction. As illustrated in FIG. 17 for the multifunctional device 210, the outer member 212 and the inner member 214 have segments 261 formed with a predetermined bend or angle, only the segment 261 for outer member 212 being visible in FIG. 17. Segment 261 includes a portion of the length of outer member 212 and can be designed in many various ways to normally assume the predetermined bend or angle. For example, the segment 261 can be made of a shape memory material or can include a directional bias, hinges or joints. The segment 261 is designed to be maintained in a straight configuration when disposed within the outermost member 212' in the non-deployed position and to assume the predetermined bent configuration in an adjusted position upon extension of the segment 261 from outermost member 212'. Accordingly, with the segment 261 in the predetermined bent configuration, the loop forming portion 216 will be disposed at an angle with a longitudinal axis of the multifunctional device 210.

Figure 18:
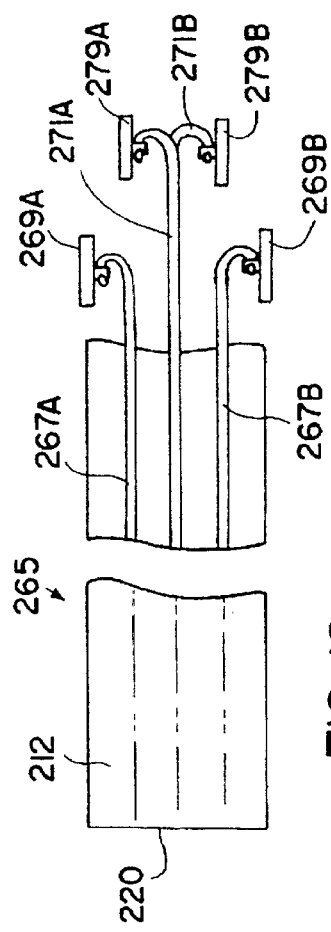
FIG. 18 is a schematic top view of an adjustment system for the multifunctional devices according to the present invention.
Figure 19:
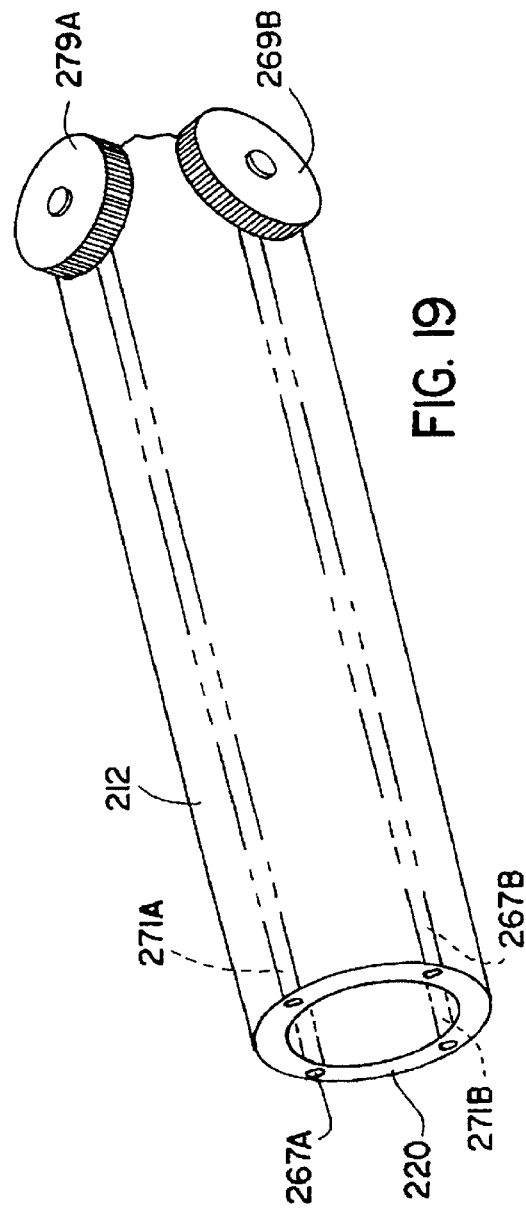
FIG. 19 is a perspective view of the adjustment system of FIG. 18 in combination with the inner member of the multifunctional device of FIG. 12.

FIGS. 18 and 19 illustrate an adjustment system 265 for moving the multifunctional devices to an adjusted position to change the orientation or direction of the distal portion of the multifunctional devices during use where one or both of the elongate members is made of flexible or bendable material. The adjustment system 265 is illustrated in FIGS. 18 and 19 in conjunction with the outer member 212; however, it should be appreciated that the adjustment system can be utilized with any elongate member forming part of the multifunctional devices. Adjustment system 265 includes left and right control wires 267A and 267B extending lengthwise along the outer member 212 within the wall forming outer member 212 or within recesses along an outer surface of the wall. Wires 267A and 267B are disposed on opposing lateral sides of outer member 212 and have distal ends connected with the outer member distal end 220 and proximal ends connected with left and right control wheels 269A and 269B, respectively. Upper and lower control wires 271A and 271B extend along the outer member 212 at opposing upper and lower sides thereof. Upper and lower control wires 271A and 271B extend through the wall forming outer member 212 or within recesses along an outer surface of the wall. Wires 271A and 271B have distal ends connected with the outer member distal end 220 and proximal ends connected with upper and lower control wheels 279A and 279B, respectively. Control wheels 269 and 279 can be mounted at various locations on the multifunctional device to be easily operated, preferably by the hand grasping the handle assembly, and the control wheels 269 and 279 can be mounted on the outer member 212 or the handle assembly, for example. The control wires 267 and 271 are movable proximally and distally in response to winding or rotation in a first direction of wheels 269 and 279 and in response to unwinding or rotation in a second direction of wheels 269 and 279. Accordingly, the control wires 267 and 271 are wound or shortened, and unwound or lengthened around pins or axles of the control wheels. Movement of one or more wires 267 and 271 by the control wheels results in a corresponding force being applied to outer member 212 due to connection of the wires at the outer member distal end 220. Therefore, winding or pulling of left control wire 267A in the proximal direction by left control wheel 269A will cause the distal end 220 to move to the left, looking proximally at FIG. 19, and pulling of right control wire 267B by right control wheel 269B will cause the distal end 220 to move to the right. Pulling of upper and lower control wires 271A and 271B in the proximal direction by upper and lower control wheels 273A and 273B, respectively, will cause the distal end 224 to move up or down. It will be appreciated that various combinations of movements as permitted by the control wires can be used to adjust the orientation of the elongate member distal end. Distal movement of the control wires via unwinding by the control wheels will result in reverse movements of the elongate member to straighten the elongate member longitudinally. The control wheels can be provided with various mechanisms, such as releasable ratchet mechanisms, for locking the position of the control wheels to maintain the adjusted position for the elongate member. It should also be appreciated that the control wires can be operated in various ways in addition to the control wheels and that more than one directional adjustment can be obtained with a single control wheel.

A modification of a multifunctional device according to the present invention is illustrated in FIGS. 20 and 21 at 310, the handle assembly for the multifunctional device 310 not being shown. Multifunctional device 310 is similar to multifunctional device 210 except that loop forming portion 316 for multifunctional device 310 forms a predetermined bent configuration in a partially deployed position. Upon movement of one or both of the outer member 312 and the inner member 314, loop forming portion 316 will be in the partially deployed position wherein strips 330 are bent outwardly at joints or bend or fold lines 381. Joints 381 are centrally located along the length of strips 330 causing the strips 330 to protrude or bulge in a direction outwardly of a longitudinal axis of the multifunctional device 310. Joints 381 can be formed as hinges or pivots, which can be formed integrally unitarily with strips 330 or as separate components. Depending on the material utilized for strips 330, the opposing ends of strips 330 can be pivotally attached to the distal end 320 of the outer member 312 and the distal end 324 of the inner member 314 at joints, hinges or pivots. The strips 330 can be provided with or without a spine for guiding the strips 330 to assume the predetermined configuration in the partially deployed position shown in FIG. 20. The strips 330 can be designed to assume the predetermined configuration shown in FIG. 20 when in the partially deployed or intermediate deployed position and to assume a predetermined or non-predetermined full loop configuration, such as that shown in FIG. 14, when in a fully deployed position upon further movement of the outer member 312 and/or the inner member 314.

As shown in FIG. 21, the inner member 314 is provided with one or more holes or apertures 383 communicating with the lumen of the inner member 314. Accordingly, suction can be applied through the lumen of the inner member 314 for withdrawing substances absorbed or collected by the loop forming portion 316, and the suction can be applied in combination with wringing or twisting of the loop forming portion 316 via rotation of one or both of the outer member 312 and the inner member 314. It should be appreciated that apertures 383 can also be utilized to introduce various materials, such as medicaments, into the body through the multifunctional device 310.

Another modification of a multifunctional device according to the present invention is illustrated in FIG. 22 at 410 wherein the handle assembly for multifunctional device 410 is not shown. Multifunctional device 410 is similar to the multifunctional devices previously described except that loop forming portion 416 for multifunctional device 410 includes a plurality of strips 430 having connecting segments 485 extending between the strips 430 and one of the elongate members. Each strip 430 has a first end connected to a distal end 420 of outer member 412 and a second end connected to a distal end 424 of inner member 414 and a connecting segment 485 connected between the strip 430 and the outer member distal end 420. The outer member 412 and inner member 414 can be arranged in the non-deployed position to position loop forming portion 416 within the outer member 412 as described for multifunctional device 10 or externally of the outer member 412 as described for multifunctional device 210. Upon relative movement of the outer member 412 and/or the inner member 414, the loop forming portion 416 will be moved to the deployed position shown in FIG. 22 wherein the connecting segments 485 guide, maintain or strengthen the strips 430 to form a predetermined loop configuration. Accordingly, connecting segments 485 can serve as a re-enforcement or spine for the strips 430. Additionally, the strips 430 can be designed in many various ways, such as with a shape memory or bias, to be urged away from the connecting segments 485 in the deployed position creating spaces or interstices 487 within the loops formed by strips 430. Accordingly, the strips 430 can form an enlargement or protrusion of increased size and can promote increased absorption by loop forming portion 416 as well as increased collection of fluid and/or tissue within interstices 487.

Another modification of a multifunctional device according to the present invention is illustrated at 510 in FIG. 23 wherein the handle assembly for the multifunctional device 510 is not shown. Multifunctional device 510 includes a loop forming portion 516 made up of a single strip 530 having a first end attached to the distal end 520 of outer member 512 and a second end attached to the distal end 524 of inner member 514. In a non-deployed position, the outer member 512 and the inner member 514 can be positioned relative to one another to position the loop forming portion 516 within the outer member 512 or externally of the outer member 512. In response to relative movement of one or both of the outer member 512 and inner member 514, the loop forming portion 516 is moved to the deployed position illustrated in FIG. 23 wherein the strip 530 forms a loop, which can be rigid or flexible, to serve as a protruding probe or finger for performing various functions in the body.

An additional modification of a multifunctional device according to the present invention is illustrated in FIG. 24 at 610 wherein the handle assembly for the multifunctional device 610 is not shown. Multifunctional device 610 includes a loop forming portion 616 made up of a plurality of strips 630 connected between outer member 612 and inner member 614 as previously described. In a deployed position as shown in FIG. 24, the strips 630 assume a multiple loop configuration. During use within the body, one or more of the strips 630 can be cut or detached; and, as shown in FIG. 24, a first end of one of the strips 630' has been detached from its point of connection with the distal end 620 of the outer member 612. Strip 630' thusly provides an elongate, distally extending narrow probe for performing various functions and procedures in the body. As further shown in FIG. 24, the strips 630 each include a passage 689 therethrough which, upon detachment of a strip 630 from the outer member 612 or the inner member 614, can be utilized for fluid flow to introduce substances in and to withdraw substances from the body via the passage 689. Passages 689' can be provided through the wall of outer member 612 or inner member 614 for communicating with supplemental conduits, such as that shown in FIG. 29, and with the passages 689 for allowing flow through device 610 via strips 630.

FIG. 25 illustrates a modification of a multifunctional device 710 according to the present invention in combination with a suction cutter assembly 766. Multifunctional device 710 is similar to multifunctional device 10 except that the handle assembly 718 for multifunctional device 710 includes flange 722 at a proximal end of outer member 712 and flange 728 carried by inner member 714. Flanges 722 and 728 are utilized as described for multifunctional device 210 to move the outer member 712 and the inner member 714 relative to one another to move the loop forming portion 716 to the deployed position illustrated in FIG. 25. It should be appreciated that the handle assembly 718 can be provided with various locking mechanisms, if desired, for fixing the relative position of the flanges 722 and 728. The inner member 714 terminates proximally at a knob 726 for rotating the inner member within the outer member to wring or twist loop forming portions 716 with the lumen of inner member 714 at knob 726 providing an opening for insertion of suction cutter assembly 766. The suction cutter assembly 766 is similar to suction cutter assembly 66 and includes an outer member 790 and an inner member 792 mounted for longitudinal movement relative to one another by handle assembly 794. Additionally, the inner member 792 is mounted for rotation within the outer member 790 as obtained via rotation of actuating knob 743 carried on the inner member 792.

The suction cutter assembly 766 can be assembled with the multifunctional device 710 prior to introduction in the body at which time the loop forming portion 716 will be in the non-deployed position disposed within outer member 712, and the distal portion 796 of the suction cutter assembly will be disposed within the outer member 712. Upon movement of flanges 722 and 728, the loop forming portion 716 will be moved to the deployed position shown in FIG. 25 thusly exposing the distal portion 796 of the suction cutter assembly. Accordingly, the loop forming portion 716 forms a configuration of multiple loops disposed about the suction cutter assembly with the distal portion 796 of the suction cutter assembly protruding distally from the center of loop forming portion 716. Suction can be applied via the apertures 102 and 111 of the suction cutter assembly, and the cutting edges of the distal portion 796 can be utilized to cut anatomical tissue in response to relative movement of the outer member 790 and the inner member 792 via squeezing operation of handle assembly 794 or via rotational movement of inner member 792 via knob 743.

A modification of a suction cutter assembly according to the present invention is illustrated at 866 in FIG. 26. Suction cutter assembly 866 is similar to the suction cutter assemblies previously described except that outer member 890 is covered by a layer of absorbent material 895 along distal portion 896. Suction cutter assembly 866 includes outer member 890 terminating distally at a blunt, rounded distal end and inner member 892 disposed in outer member 890 and terminating distally at a blunt, rounded distal end corresponding to the distal end of outer member 890. As best shown in FIG. 27, the distal portion of outer member 890 includes a plurality of apertures 902 defining cutting edges 900, and the inner member 892 includes a plurality of apertures 911, normally aligned with the apertures 902, defining cutting edges 908. Apertures 902' and 911' are provided at the distal ends of the outer and inner members, respectively, define a central passage or channel communicating with the lumen of the inner member 892. The layer of material 895 includes a plurality of apertures 897 aligned with the apertures 902 in the outer member 890.

A modification of a handle assembly for use in either the multifunctional devices or collection systems of the present invention is illustrated at 918 in FIG. 28. Handle assembly 918 is desirable for longitudinally moving one elongate member relative to another elongate member and for rotating one elongate member relative to another elongate member. The handle assembly 918 is described in connection with an outer member 912 and an inner member 914; however, it should be appreciated that the handle assembly 918 can be utilized with any elongate members for which relative longitudinal movement and/or rotational movement is desired. Handle assembly 918 includes an elongate hollow housing 997 defining a passage for receiving a transverse flange 922 at a proximal end of the outer member 912. The passage in housing 997 is defined by an internal wall 999 of housing 997 with the wall 999 having a configuration corresponding to the peripheral configuration of flange 922. A thread 1000 is provided along the internal wall 999 for cooperatively engaging an external thread 1001 along the periphery of flange 922. A transverse flange 928 carried on the inner member 914 is received in a recess in a rearward wall of housing 997. The inner member 914 terminates proximally at an actuating knob 926 disposed proximally of housing 997, and a tube 958 of inlet assembly 956 extends into the lumen of inner member 914. Inlet assembly 956 includes a hub 1002 having a truncated conical configuration disposed in abutment with actuating knob 926. Hub 1002 has an internal lumen or passage communicating with the lumen of tube 958 and a valve 960 is coupled with the passage through hub 1002.

In use, handle assembly 918 is operated by rotating the housing 997 in a first direction which causes longitudinal proximal movement of outer member 912 relative to inner member 914 as permitted by threads 1000 and 1001. Rotation of the housing 997 in an opposite, second direction causes longitudinal distal movement of outer member 912 relative to inner member 914. Rotation of housing 997 also causes rotation of outer member 912 relative to inner member 914; and, additionally, the inner member 914 is rotatable relative to the outer member 912 in response to rotation of actuating knob 926.

Figure 29:
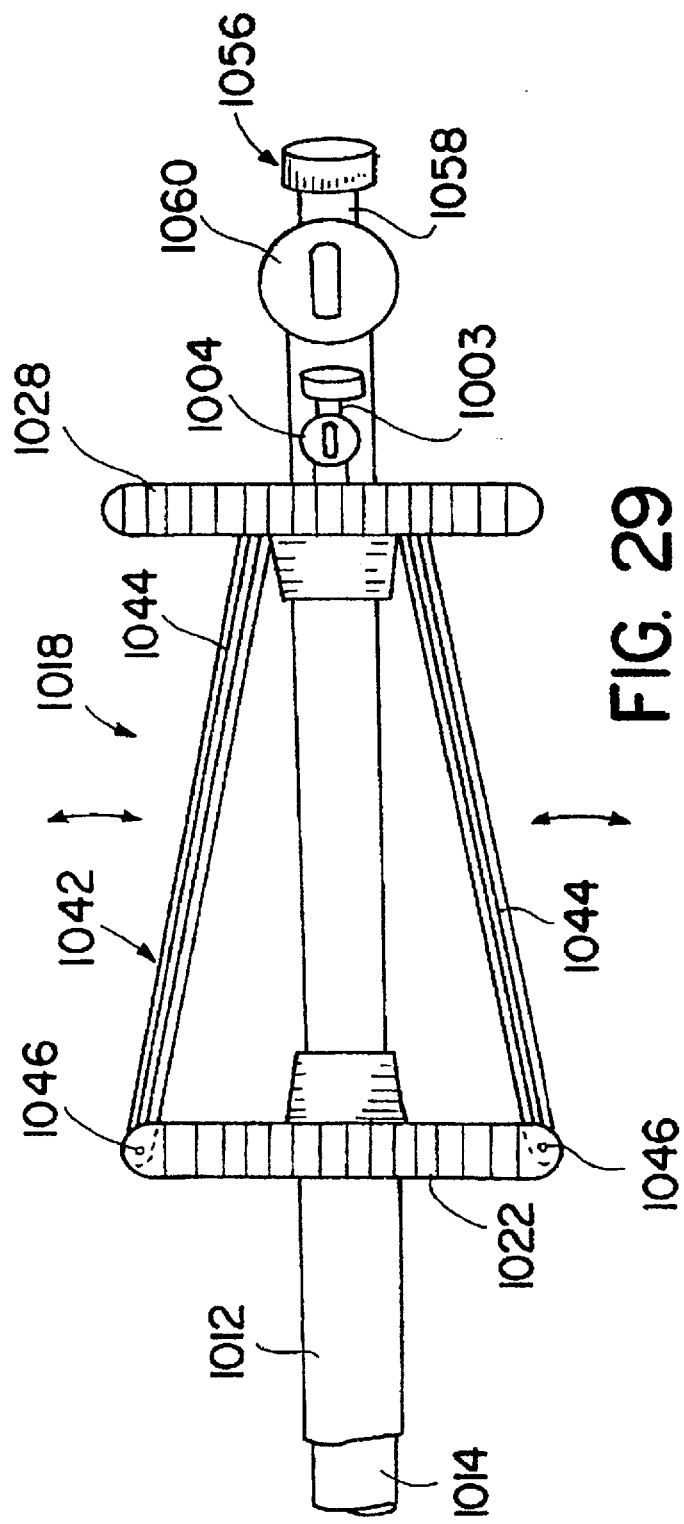
FIG. 29 is a broken side view of another modification of a handle assembly for use in the present invention.

Another modification of a handle assembly for use with the multifunctional devices and collection systems of the present invention is illustrated at 1018 in FIG. 29. The handle assembly 1018 is illustrated in conjunction with an outer member 1012 and an inner member 1014; however, it should be appreciated that the handle assembly 1018 can be utilized with any elongate members of the multifunctional devices and collection systems of the present invention. Handle assembly 1018 is similar to handle assembly 218 except that the locking mechanism 1042 for the handle assembly 1018 includes a pair of pivotable locking bars 1044. Handle assembly 1018 includes a transverse flange 1022 carried by outer member 1012 and a transverse flange 1028 carried by inner member 1014. An inlet assembly 1056 is coupled with the lumen of inner member 1014 and includes a tube 1058 extending into or formed as part of the inner member 1014, a valve 1060 for opening and closing the lumen of inner member 1014 and a supplemental conduit 1003 extending through a wall of inner member 1014 or a wall of tube 1058 for communicating with the lumen of the inner member 1014. The conduit 1003 is provided with a valve 1004 for controlling flow therethrough and, therefore, through the lumen of inner member 1014. The locking mechanism 1042 for handle assembly 1018 includes a pair of locking bars 1044 pivotally attached to flange 1022 at pivots, hinges or joints 1046. Joints 1046 are disposed at opposing lateral sides of flange 1022, and the joints 1046 can be provided with torsion springs (not shown) for rotationally biasing the locking bars 1044 inwardly in the direction of a longitudinal axis of the inner member 1014. With the locking bars 1044 rotated or biased inwardly about joints 1046, ends of the locking bars 1044 opposite the joints 1046 will engage flange 1028 to prevent movement of flanges 1022 and 1028 toward one another and thusly establishing an initial position for elongate members 1012 and 1014. When it is desired to operate handle assembly 1018 to move outer member 1012 relative to inner member 1014, the locking bars 1044 are pivoted or rotated outwardly about joints 1046 to disengage the ends from flange 1028 at which time the flanges 1022 and 1028 can be moved toward one another thusly moving the outer member 1012 and the inner member 1014.

Inasmuch as the present invention is subject to many modifications, variations and changes in detail, it is intended that all subject matter discussed above or shown in the drawings be interpreted as illustrative only and not to be taken in a limiting sense.

What is claimed is:

1. A collection system for collecting substances in the body of a patient in operative procedures wherein access to an internal operative site in the patient's body is gained through a narrow portal in the patient's body comprising a cutter having a distal end for being disposed at the operative site through the portal, a proximal end for being disposed external of the patient's body, a cutting edge at said distal end for cutting anatomical tissue and a handle at said proximal end for moving said cutting edge to cut the anatomical tissue; and a collection bag disposed over said distal end of said cutter and having a closed distal end, a proximal end fixedly attached to said cutter, an interior receiving said cutting edge and a selectively openable access slot providing communication with said interior of said collection bag from external thereof, said collection bag being movable, from external of the patient's body, from a collapsed position facilitating introduction of said collection bag at the operative site simultaneously with introduction of said distal end of said cutter at the operative site to an expanded position after introduction of said collection bag and said distal end of said cutter at the operative site to allow substances to be introduced in said interior of said collection bag through said access slot to be cut by said cutter.

2. A collection system as recited in claim 1 and further including a lumen coupled with said interior of said collection bag and connectable with a source of suction for withdrawing substances introduced in said interior of said collection bag from the patient's body.

3. A collection system as recited in claim 2 wherein said lumen extends through said cutter.

4. A collection system as recited in claim 1 wherein said collection bag includes a resilient spine for mechanically guiding said collection bag to said expanded position.

5. A collection system as recited in claim 1 wherein said access slot includes a closure for selectively opening said access slot to allow substances to be introduced in said interior and for selectively closing said access slot to confine the substances in said interior of said collection bag.

6. A collection system as recited in claim 5 wherein said closure includes a slide closure.

7. A collection system for collecting substances in the body of a patient in operative procedures wherein access to an internal operative site in the patient's body is gained through a narrow portal in the patient's body comprising a cutter including an elongate outer tubular member having a distal end for being introduced at the operative site through the narrow portal and a proximal end for being disposed external of the patient's body, a first cutting edge carried by said distal end of said outer tubular member, an elongate inner tubular member disposed in said outer tubular member and having a second cutting edge for cooperating with said first cutting edge to cut anatomical tissue and having a proximal end for being disposed external of the patient's body, said outer tubular member and said inner tubular member being movable relative to one another, and a handle at said proximal ends of said outer and inner tubular members for moving at least one of said outer and inner tubular members relative to the other of said outer and inner tubular members to move at least one of said first and second cutting edges past the other of said first and second cutting edges to cut anatomical tissue between said first and second cutting edges; and a collection bag enclosing an interior and being fixedly attached to said outer tubular member with said first and second cutting edges disposed in said interior of said collection bag, said collection bag having an opening therein providing access to said first and second cutting edges from external of said collection bag, said collection bag being movable, from external of the patient's body, from a collapsed position facilitating introduction of said collection bag at the operative site simultaneously with introduction of said first and second cutting edges at the operative site to an expanded position after introduction of the collection bag and the first and second cutting edges at the operative site to allow substances to be introduced in said interior of said collection bag through said opening to be cut by said first and second cutting edges.

8. A collection system as recited in claim 7 wherein said outer and inner tubular members are rotatable relative to one another.

9. A collection system as recited in claim 7 wherein said outer and inner tubular members are longitudinally movable relative to one another.

10. A collection system as recited in claim 7 wherein said inner tubular member defines a lumen therethrough connectable with a source of suction for withdrawing substances introduced in said interior of said collection bag from the patient's body.

* * * * *